United States Patent [19]
Bottenstein

[11] Patent Number: 5,276,145
[45] Date of Patent: Jan. 4, 1994

[54] METHODS AND COMPOSITIONS; PURIFIED PREPARATION OF NEURAL PROGENITOR REGULATORY FACTOR

[75] Inventor: Jane E. Bottenstein, League City, Tex.

[73] Assignee: Board of Regents, University of Texas, Austin, Tex.

[21] Appl. No.: 852,755

[22] Filed: Mar. 17, 1992

Related U.S. Application Data

[63] Continuation of Ser. No. 389,841, Aug. 4, 1989, abandoned.

[51] Int. Cl.$^5$ ............... A61K 37/02; A61K 37/36; C07K 3/02; C07K 15/06
[52] U.S. Cl. ............... 530/399; 530/350
[58] Field of Search ............... 530/350, 399; 514/12, 514/21, 2, 8

[56] References Cited

U.S. PATENT DOCUMENTS 4,861,757 8/1989 Antoniades et al. ............... 514/21
5,011,914 4/1991 Collins et al. ............... 530/399

OTHER PUBLICATIONS

R. Hardy and R. Reynolds, "Rat Cerebral Cortical Neurons in Primary Culture Release a Mitogen Specific for Early ($G_{D3}$ +/04-) Oligodendroglial Progenitors" J. Neurosci. Res. 34:589-600 (1993).
Raines et al, pp. 89-109 from *Methods for Preparation of Media, Supplements, and Substrata for Serum-Free Animal Cell Culture*, Alan R. Liss, Inc. NY, NY, 1984.
Chemical Engineering, Feb. 18, 1985, pp. 154-158.
Benveniste et al, Nature 321:610-613(1986).
Eccelston et al, Developmental Brain Research 21:315-318 (1985).
Benveniste et al, Proc. Nat'l. Acad. Sci. USA 82:3930-3934 (1985).
Bosch et al, pp. 125-137 from *Model Systems of Development and Aging of the Nervous System*. Vernadakis et al, eds. (1987).
McMorris et al, J. Neuroscience Research 21:199-209(1988).
Nobel et al, Nature 333:560-562 (1988).
Mercanti et al, Experimental Cell Research 168:182-190(1987).
Huang et al, Biochem. Biophys. Research Communications 144:81-87 (1987).
Hunter et al, Abstract from Society Neuroscience, Nov. 16-21, 1987; Reference 59.8.
Bottenstein et al, J. Neurochemistry 48:Suppl (1987), Abstract #A.
Levine, Neuron 3:103-113 (1989).
Ratner et al, Proc. Nat'l Sci USA 85:6992-6996(1988).
Bottenstein et al, "CNS Neuronal Cell-Line-Derived Factors...". J. Neuroscience Res. 20(3):291-303(1988).
Hunter et al, "Responses of Neonatal and Adult Glial Progenitors...". Society for Neuroscience, Abstract No. 132.13 (1988).
Armstrong et al, "In Vitro Analysis of the Oligodendrocyte Lineage...". J. Cell Biology, vol. III, Sep. 1990. pp. 1183-1195.
Besnard et al, "Platelet-derived growth factor is a mitogen for glial...". Neuroscience Letters, 73 (1987). pp. 287-292.
Chan et al, "Oligodendrocyte-type 2 astrocyte progenitor cells from neonatal...". Developmental Brain Res., 55(1990) 275-82.

(List continued on next page.)

Primary Examiner—Jeffrey E. Russel
Attorney, Agent, or Firm—Arnold, White & Durkee

[57] ABSTRACT

A novel substantially purified preparation of a neural progenitor regulatory factor and methods for producing such purified factor are claimed. In a preferred embodiment, the factor has an approximate molecular weight of about 46-47 kilodaltons (as determined by SDS polyacrylamide gel electrophoresis), has affinity for heparin, and stimulates proliferation of 0-2A glial progenitor cells.

5 Claims, 14 Drawing Sheets

OTHER PUBLICATIONS

Hart et al, "PDGF and Intracellular Signalling in the timing . . . ". *J. Cell Biology*, vol. 109 (No. 6, Pt. 2) Dec. 1989. pp. 3411–3417.

Hunter et al, "0-2A Glial Progenitors from Mature Brain Respond to . . .". *J. Neuroscience Res.*, vol. 27 (1990).

Hunter et al, "Bipotential glial progenitors are targets of . . . ", *Developmental Brain Research*, vol. 49 (1989). pp. 33–49.

Riss et al, "Human Recombinant Insulin-Like Growth Factor I . . . ".*In Vitro Cell. & Devel. Biol.* vol. 24, No. 11, Nov. 1988. pp. 1099–1106.

Smith et al, "Growth factors adherent to cell substrate are mitogenically active in situ". *Nature*, vol. 296. Mar. 11, 1982. pp. 154–155.

LaRochelle et al, "Immunochemical Localization of the Epitope . . . ". *Molecular and Cell. Biol.*, vol. 9, No. 8, Aug. 1989. pp. 3538–3542.

Kiess et al, "Rat C6 Glial Cells Synthesize Insulin-like Growth Factor I . . . ". *Endocrinology*, vol. 124, No. 4. 1989. pp. 1727–1736.

Gospodarowicz et al., "Fibroblast growth factor in the human placenta, " Biochem. Biophys. Res. Comm., 128:554–562 (1985).

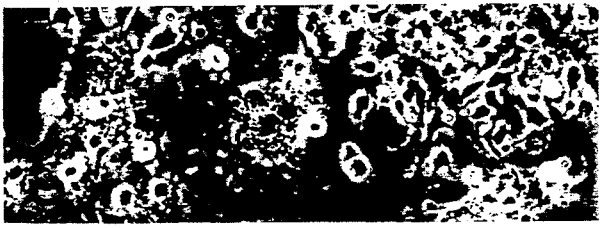

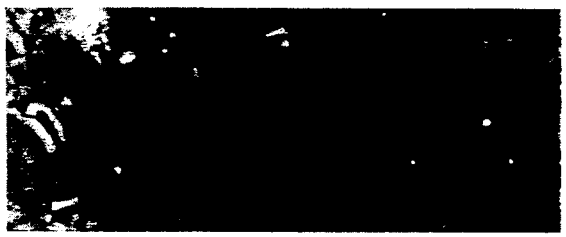

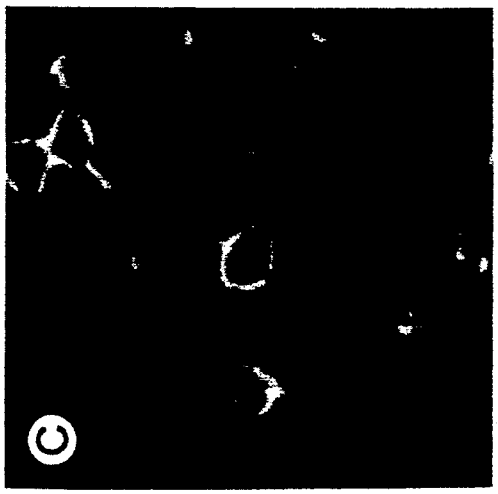
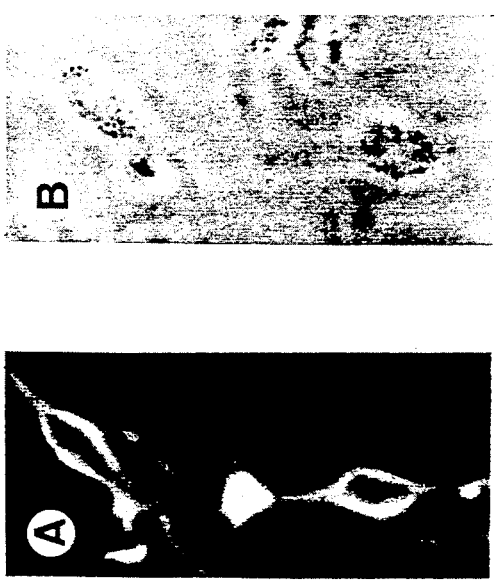
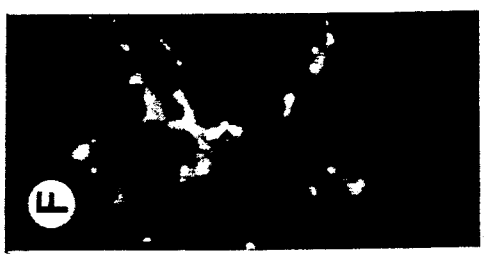

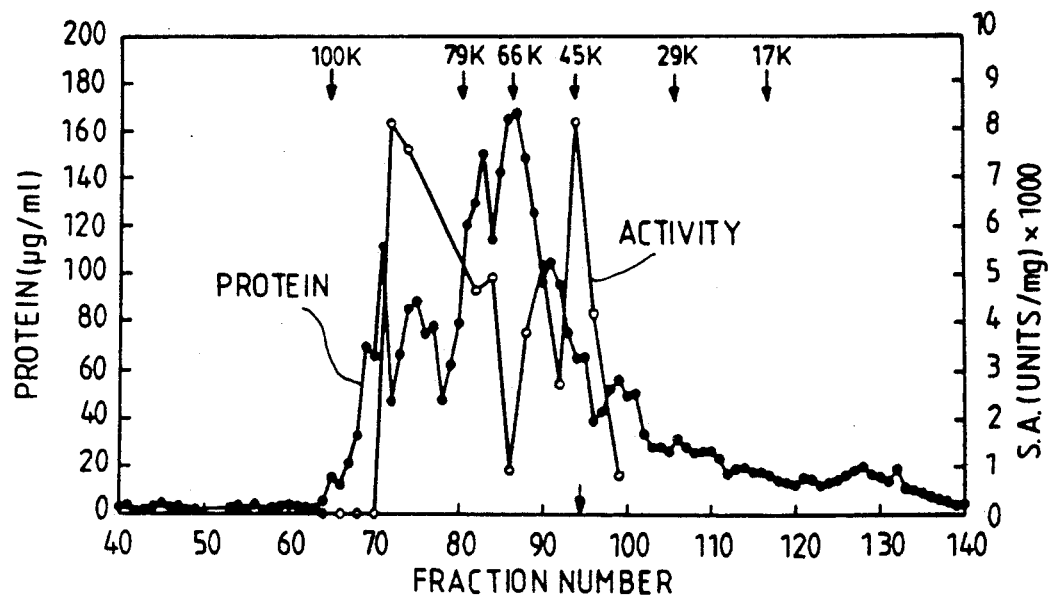
FIG. 17A SEPHACRYL S-200 COLUMN I (A2B5)
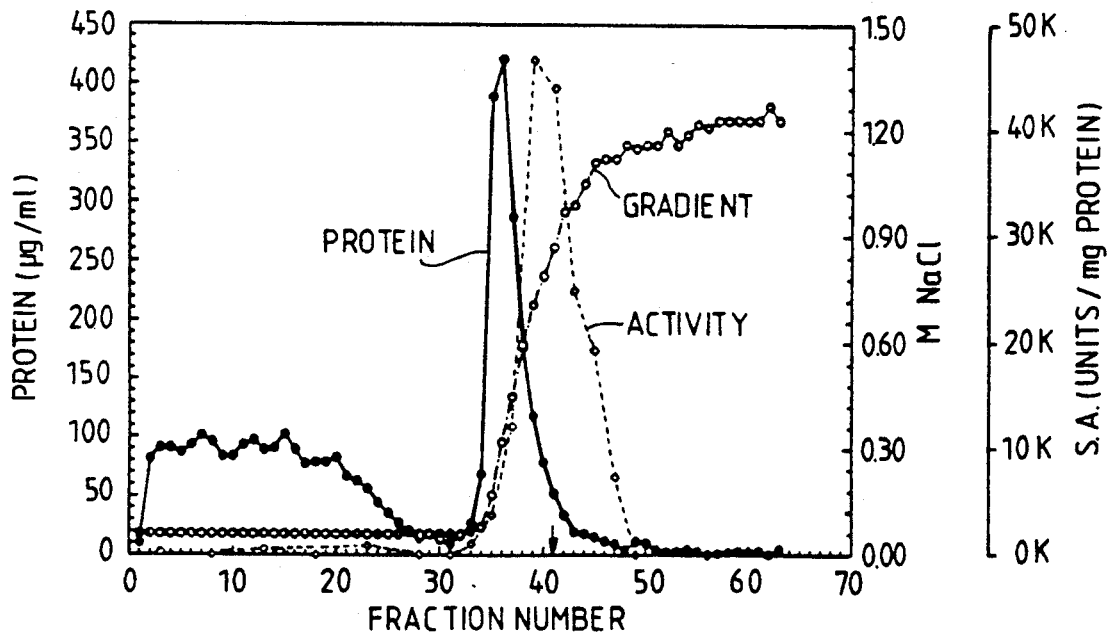
FIG. 17B ELUTION PROFILE OF HEPARIN-SEPHAROSE COLUMN VI (A2B5)

FIG. 19

SERUM-FREE CONDITIONED MEDIUM (CM)
FROM MICROCARRIER CULTURE
OF B104 CELLS

↓

CONCENTRATION/DIALYSIS (C/D) AGAINST PBS
OF B104 CM WITH AMICON DC-2 HOLLOW FIBER UNIT
WITH CUTOFF OF 10000 DALTONS

↓ ↓ ↓

SEPHACRYL S-200 I

ACTIVE FRACTION AT 46-57 KD

CL-6B HEPARIN-SEPHAROSE VI

ACTIVE FRACTION ELUTES WITH 0.7-0.8 M NACL

10% SDS-PAGE GEL  →ELUTION→

COMMON 47 KD BAND IN LANES WITH CM, C/D, S-200 I, AND HEP V

ACTIVE FRACTION AT 45-50 DK IN MTT ASSAY; 11% INCREASE OVER CONTROL ($P=0.03$ BY STUDENT'S TEST)

LEGEND:

SODIUM DODECYL SULFATE-POLYACRYLAMIDE (SDS-PAGE) MINIGEL ELECTROPHORESIS: SAMPLE WAS CONCENTRATED 10X BY ULTRAFILTRATION (10000K CUTOFF); 4% STACKING GEL; 10% SEPARATING GEL; RUNNING BUFFER TRIS-HCL pH 8.3; 150-180 VOLTS; SILVER STAIN TO VISUALIZE PROTEINS.

ELUTION FROM SDS-PAGE GEL: PERFORMED BY SLICING MINIGEL LANES CONTAINING C/D III INTO 2.5 MM SEGMENTS, WASHING TWICE WITH 1 ML COLD PBS, AND ELUTING 2 SLICES TOGETHER OVERNIGHT WITH SHAKING AT 4 DEGREES C IN 150 MICROLITERS OF PBS. LOW ACTIVITY IS RESULT OF INCOMPLETE ELUTION AND THE PRESENCE OF RESIDUAL SDS. MOLECULAR WEIGHT RANGES OF SLICES WERE DETERMINED AGAINST PRESTAINED MARKERS RUN ON THE GEL.

METHODS AND COMPOSITIONS; PURIFIED PREPARATION OF NEURAL PROGENITOR REGULATORY FACTOR

FUNDING

Development of the present invention was facilitated by funding from the National Institutes of Health, Grant # NS 20375. Accordingly, the U.S. Government may own certain rights.

This application is a continuation of application Ser. No. 07/389,841, filed Aug. 4, 1989, now abandoned.

FIELD OF THE INVENTION

The present invention relates to substantially purified preparations containing a proteinaceous factor—termed neural progenitor regulatory factor—that is important in regulating and coordinating production of oligodendrocytes and type 2 astrocytes. The primary target of the factor is the bipotential glial progenitor cell, which gives rise to oligodendrocytes and type 2 astrocytes. Therapeutic implications for use of the factor include: (1) stimulation in vivo of glial progenitor cell division, followed by remyelination of axons in demyelinating disorders such as multiple sclerosis, and regeneration after trauma to the Central Nervous System; (2) amplification of glial progenitor cells in culture, followed by transplantation into the central nervous system and subsequent remyelination and regeneration; and (3) increase in neuronal cell number, facilitating recovery in neurodegenerative disorders.

DESCRIPTION OF THE RELATED ART

The major types of glial cells in the Central Nervous System are type 1 astrocytes, type 2 astrocytes, and oligodendrocytes (Fedoroff, 1985; Williams et al., 1985). While there is a wealth of information about the regulation of type 1 astrocyte cell division, there is much less known about type 2 astrocyte or oligodendrocyte proliferation. The two latter cell types appear to share a common bipotential progenitor cell, designated as an O-2A cell by Raff et al. (1983). This bipotential progenitor cell has been identified in newborn and adult rat optic nerve (ffrench-Constant and Raff, 1986) and in postnatal day 8 rat cerebellar cultures (Levi et al., 1986).

An ability to understand and regulate proliferation and differentiation of this bipotential progenitor is likely to prove critical in development of a rational therapeutic regime for treatment of demyelinating disorders, such as multiple sclerosis or treatment of traumatic injury to the CNS.

In the past, several investigators have attempted without success to identify well-characterized growth factors that stimulate oligodendrocyte production (Pruss et al., 1982; Brockes et al., 1980). Others, however, have reported soluble factors active on cells of the Central Nervous System. For example, Noble and Murray reported that soluble factors produced by type 1 astrocytes stimulate proliferation of O-2A progenitor cells (Noble and Murray 1984), and it has been suggested that at least one such factor is identical to Platelet-derived growth factor (Noble, et al., 1988). In addition, two T-lymphocyte-derived growth factors have been reported to induce division of oligodendrocytes (Benveniste, et al, 1985, Benveniste and Merrill, 1986).

Avendano and Cowan (1979) provided indirect support for neuronal factor regulation of oligodendrocyte growth in vivo. Those investigators found that morphologically identified oligodendrocytes proliferate in response to lesions of the ventral hippocampal commissure. They suggested that since a substantial proportion of these cells increased outside the axonal degeneration area, the axons released a diffusible mitogen which stimulated the increase locally as well as at a distance. Pettman et al. (1980) first reported that neuron-enriched embryonic brain extracts increase the number of oligodendrocyte-like cells in newborn rat brain cultures. More recently, Giulian and Young (1986) described two different neuron-derived soluble factors of low molecular weight (15,000 and 6,000) found in both the CNS and the peripheral nervous system (PNS) that increase oligodendrocyte cell numbers in culture. Sakellaridis et al. (1986) reported that conditioned medium from chick embryo neuronal cultures increased the expression of an oligodendrocyte marker (3',5'-cyclic nucleotide 3'-phosphodiesterase; Kurihara and Tsukada, 1968) in corresponding glial cultures. Both soluble and particulate fractions from purified chick neuronal cultures have been reported to increase the number of rat brain oligodendrocytes (Edgar and Pfeiffer, 1985). Finally, although PNS axon-derived molecules have been shown to stimulate progenitors of 1-2-week-old and adult oligodendrocytes to divide in vitro (Wood and Williams, 1984; Wood and Bunge, 1986), CNS axon-derived molecules have not yet been shown to be similarly active.

Recently, the present inventor reported that proliferation of oligodendrocyte precursors could be enhanced by culture in a medium supplemented with conditioned medium from culture of the rat CNS B-104 neuroblastoma cell line (Bottenstein and Hunter 1987; Hunter et al., 1987). However, the activity was neither purified nor characterized biochemically and its mechanism of action was not determined. The present inventor has now characterized that activity and discovered a proteinaceous molecule of about 47 kilodaltons in weight that regulates proliferation of O-2A progenitor cells. This novel factor has been distinguished from other factors reported to induce the growth of cells derived from the CNS.

SUMMARY OF THE INVENTION

As indicated above, the present inventor has now, for the first time, devised a method allowing one to achieve a substantial purification of the neural progenitor regulatory factor and to determine certain biochemical characteristics of the neural progenitor regulatory factor, such as its molecular weight and sensitivity to various chemical treatments. Therefore, the present invention encompasses both a substantially purified preparation of the factor and methods suitable for achieving such purification.

More specifically, the invention includes a composition of matter comprising a substantially purified preparation of a neural progenitor regulatory factor. The factor may be characterized as having a molecular weight greater than about 30 kilodaltons as determined by sodium dodecyl sulphate polyacrylamide gel electrophoresis and as possessing the ability to stimulate proliferation of. O-2A glial progenitor cells. In more specific embodiments, the characteristic molecular weight will fall between about 40 and about 50 kilodaltons, and in a most specific embodiment, around about 46–47 kilodaltons, as determined by SDS polyacrylamide gel electrophoresis.

The neural progenitor regulatory factor can be distinguished from another protein reported to exhibit biologic effects on glial progenitor cells, Platelet Derived Growth Factor (PDGF) since its molecular weight is substantially greater than the reported molecular weight of PDGF, 30 kilodaltons. The factors may be further distinguished by immunologic criteria. The present inventor has discovered that incubation of the factor with an antiserum specific for platelet derived growth factor does not significantly inhibit activity of the neural progenitor regulatory factor, and hence, the two factors are classified as immunologically distinct.

Although the examples set forth below describe testing of the factor with 0-2A progenitors from neonatal rat brain, the factor has also been found active against 0-2A progenitors obtained from mature rat brain.

The present inventor has discovered that one suitable source from which the factor may be purified is the conditioned medium produced by culture of the rat CNS B-104 neuroblastoma cell line deposited with the American Type Culture Collection under Accession Number CLR 10187. Accordingly, the invention also comprises a purified preparation of a neural progenitor regulatory factor that is substantially similar to the neural progenitor regulatory factor produced by that cell line, for example, in terms of characteristic biologic activity, molecular weight, and/or immunologic distinctiveness from platelet derived growth factor and fibroblast growth factor.

Substantial purification of the factor is achieved when the factor is prepared in a form in which it is more free from protein and other contaminants than the form found in conditioned medium. A variety of methods are set forth herein that may be used to accomplish this end.

For example, the inventor has made the surprising discovery that the neural progenitor regulatory factor has affinity for heparin, and that by taking advantage of this selective affinity, one can facilitate its purification. Accordingly, the invention is also directed to a composition of matter comprising a substantially purified neural progenitor regulatory factor wherein the factor has characteristic affinity for heparin such that it binds to a heparin-sepharose gel particle when mixed together with a preparation of heparin-sepharose gel particles, in a buffer comprising 5 mM phosphate, 50 mM NaCl, and having a pH of about 7.4, for a period of about 18 hours and elutes from the heparin-sepharose gel particles when the concentration of NaCl in the buffer is raised above about 0.7 M-0.8 M. Of course, in this embodiment also, the factor is characterized as having a molecular weight of greater than about 30 kilodaltons as determined by sodium dodecyl sulphate polyacrylamide gel electrophoresis and by its ability to stimulate proliferation of 0-2A progenitor cells. In a related embodiment, the factor is characterized by its ability to stimulate proliferation of cells of the rat CNS C62B glial progenitor cell line.

The invention also comprises methods suitable for achieving a substantial purification of the factor, particularly, for example, as compared to the medium conditioned by the B104 neuroblastoma cell line. One method comprises the following steps. First, one obtains a first preparation containing the neural progenitor regulatory factor together with other protein. This preparation is produced by culturing B104 neuroblastoma cells in a suitable culture medium. The first preparation is mixed together with a solid matrix having heparin coupled thereto in a solution of such molarity of a selected salt, for example, NaCl or KCl or a suitable equivalent, that a substantial portion of the factor binds to the heparin-matrix. Then, the heparin-matrix having the factor bound thereto is washed with a solution of increasing molarity so as to selectively elute the factor from the matrix and thereby produce a second preparation. This second preparation will contain the desired factor in a form substantially more free from other proteins or contaminants than did the first preparation.

A second method which has also been used successfully comprises the following. As before, one obtains a first preparation containing the neural progenitor regulatory factor mixed together with other protein by culturing B104 neuroblastoma cells in a suitable culture medium. Then one fractions the preparation by gel exclusion chromatography. Although a number of gels suitable for this purpose may be used, the inventor has achieved remarkable success using Sephacryl-200. Generally, the fractions eluting from the gel are then assayed for neural progenitor regulatory factor by an assay that detects activity—that is the ability to stimulate proliferation of bipotential 0-2A glial progenitor cells or, more specifically, to stimulate the growth of the C62B glial progenitor cell line. However, other suitable assays may be devised with the aid of the present disclosure. After assay, the fractions having glial progenitor cell stimulating activity are selected and optionally, pooled together.

In a further preferred embodiment, the B104 cells will be cultured on positively charged microcarrier beads to enhance the concentration of factor in the crude conditioned medium. Moreover, although the broader claims are in no way limited by the specific type of culture medium to be used in the B104 cell culture process, the present inventor has found that a particularly effective culture medium comprises insulin, putrescine, progesterone, selenite and transferrin, but does not comprise serum. The inventor has found that a medium comprising a 1:1 mixture of Ham's F12 and Dulbecco's Modified Eagle's media supplemented with 5 $\mu$g/ml bovine insulin, 100 $\mu$M putrescine, 20 nM progesterone, 30 nM selenite, and 1 $\mu$g/ml human transferrin is particularly suitable.

Other suitable methods will combine the individual methods set forth herein. For example, a combination procedure employing both heparin affinity chromatography and gel exclusion chromatography may be used. If this is done, either may be performed first. However, a preferred embodiment includes a method for producing a purified preparation of neural progenitor regulatory factor comprising the steps of obtaining a first preparation containing the neural progenitor regulatory factor together with other protein, that preparation produced by culturing B104 neuroblastoma cells in a suitable culture medium; mixing the first preparation together with a solid matrix having heparin coupled thereto in a solution of such molarity of a selected salt that a substantial portion of the factor binds to the heparin; washing the heparin-matrix and factor bound thereto with a solution of increasing molarity so as to selectively elute the factor from the matrix and thereby produce a second preparation. The second preparation is characterized in that it contains the neural progenitor regulatory factor in a form substantially more free from the other protein than the first preparation; however, in this embodiment, the preparation is purified further by fractionating the second preparation by gel exclusion chromatography; assaying the fractions for an ability to stimulate proliferation of bipotential 0-2A glial progenitor cells; selecting fractions having glial progenitor cell stimulating activity; and optionally, pooling fractions having glial progenitor cell stimulating activity. Optionally, the pooled fractions may be purified further by performing an additional step comprising electrophoresing the selected fractions through a gel matrix in a manner such that said neural progenitor regulatory factor is localized in a band of protein, positioned in the gel at a position consistent with a molecular weight of about 46–47 kilodaltons.

Of course, the invention will include a substantially purified neural progenitor cell regulatory factor produced by any of the methods set forth above.

The invention also includes methods for stimulating proliferation of glial progenitor cells. Generally, such methods comprise the steps of obtaining a preparation of glial progenitor cells suitable for culture; and culturing those cells together with an effective amount of a substantially purified preparation of neural progenitor regulatory factor.

Finally, the invention includes a novel assay for neural progenitor regulatory factor. The assay comprises the following steps: obtaining a first preparation and a second preparation of C62B cells suitable for cell culture; culturing the first preparation in a suitable culture medium together with an effective amount of a preparation to be tested for a neural progenitor regulatory factor; and culturing the second (or control) preparation in the culture medium but without the neural progenitor regulatory factor. The growth of cells in the first and second preparation are compared and the neural progenitor regulatory factor is detected in the first preparation if the growth of progenitor cells in the first preparation is significantly increased over the growth in the second preparation.

These and other aspects of the invention will become more apparent from a description of particular embodiments when read in conjunction with the drawings.

DESCRIPTION OF THE DRAWINGS

FIG. 4A-E: Effect of conditioned medium from various donors. Neonatal rat brain cells were plated directly in O1 medium and 50% conditioned medium on polylysine and fibronectin modified surfaces and are shown after 9 days in vitro. Conditioned medium donors: A) B104 rat CNS neuroblastoma cells in N2 medium; B) CO-13-7 calf brain oligodendrocyte x C6 rat CNS glioma hybrid cells in 01 medium; C) U251 MGsp human CNS glioma cells in G2 medium; D) C62B rat CNS glioma cells in G2 medium; E) 2LI human PNS neuroblastoma cells in N2 medium. Generation of the conditioned media and the components of the serum-free media are described below.

FIG. 8: Dissociated neonatal rat brain cells shown after 13 days in vitro in various media. Cells were plated directly in 01 medium on polylysine- and fibronectin-modified culture surfaces at a density of 500,000 cells/cm$^2$ with the following additions: A) none; B) 1 mM pyruvate; C) 33% unconditioned medium (N2); D) 33% B104 conditioned medium; E) 33% B104 conditioned medium and $10^{-8}$ a M triiodothyronine.

FIG. 12A–G: Fluorescence and phase-contrast micrographs of A2B5-immunostained neonatal rat brain cell cultures. Cells were cultured in 33% B104-conditioned medium/67% O3 medium as described. (A-C) Percoll gradient-processed cells at 3 days in vitro (DIV), 6-h $^3$H-thymidine pulse (1 μCi/ml); (D-G) cells prepared without Percoll gradient-processing, 24-h $^3$H-thymidine pulse; (D,E) at 4 DIV and (F,G) at 8 DIV. Cultures were immunostained and processed for autoradiography as described. The multipolar cells in (C), plated at twice the density of those shown in (A), were rarely labeled with $^3$H-thymidine. The silver grains shown exhibit a peripheral pattern of nuclear labeling, consistent with the high nuclear/cytoplasmic ratio and peripheral chromatin organization within the nucleus of progenitor cells. The heavy labeling obscured fluorescence over the nucleus in (D) and (F). Bar = 20 microns.

FIG. 17: Chromatography of neural progenitor regulatory factor over Sephacryl S-200 and Heparin-Sepharose affinity columns. One unit of specific activity is defined as a 100% increase over control number of A2B5-positive cells after 4 days in culture/mg of protein.

FIG. 19: Flow diagram showing methods for purification of neural progenitor regulatory factor.

DESCRIPTION OF A PREFERRED EMBODIMENT

Figure 1A:
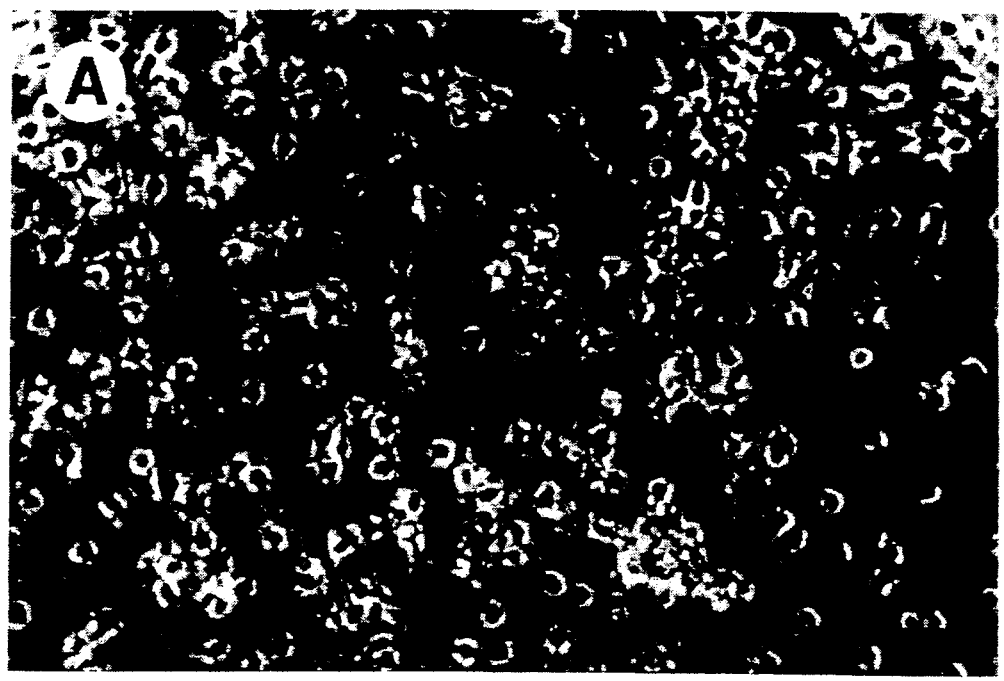
FIG. 1A-B: Morphology and galactocerebroside expression of neonatal rat brain cells after 9 days in vitro. Cells were plated at a density of $5 \times 10^5/cm^2$ in O3 medium with 33% B104 conditioned medium on polylysine- and fibronectin-modified culture surfaces. (A) phase contrast and (B) fluorescence micrograph of cells immunostained for galactocerebroside. Bar = 50 microns.

As indicated above, the present inventor has now characterized and purified a proteinaceous molecule of about 46–47 kilodaltons molecular weight that is able to selectively induce proliferation of CNS bipotential glial progenitor cells in vitro. This purified factor may be used in vitro for selective expansion of the bipotential glial progenitors prior to subsequent use of such cells, for example, for transplantation. In addition, the factor may find significant utility as a therapeutic for demyelinating disorders or in neurodegenerative disorders.

As described below, the factor was originally purified from conditioned medium produced by the CNS B104 neuroblastoma cell line of the rat. However, with the characterization and purification of the factor now described by the present inventor and in view of the teaching of the present disclosure, those of skill in the art should be enabled to identify and purify the factor from other sources, including, for example, human tissue.

The first set of examples set forth below describes experiments conclusively establishing the biological characteristics of the factor, i.e, its target cells and mode of action, for the first time. A novel, reproducible, and sensitive assay for the factor, using the C62B glial progenitor cell line, ATCC accession number CCL107, is also described. The second set of examples describes biochemical aspects of the factor and provides methodology that now makes it possible to achieve a substantial purification of the factor. The third example demonstrates that the factor characterized and described by the present inventors is distinct from other factors reported to enhance growth of CNS cells.

EXAMPLE 1

A. Methods for Culture of Oligodendrocytes and Astrocytes

Materials and Sources. Suitable materials for use in culture of bipotential progenitors may be obtained from the following vendors: high glucose Dulbecco's modified Eagle's Medium (DME; 430-2100), Ham's F12 medium (F12; 430-1700), penicillin/streptomycin/neomycin (600-5640), and gentamicin (600-5710) from GIBCO, Grand Island, NY; Hank's balanced salt solution with (HBSS$\pm$; 9222) and without (HBSS$-$; 9230) calcium and magnesium salts, trypsin (9336), EDTA (9314), and fetal bovine and calf serum from Irvine Scientific, Santa Ana, Calif.; N-2-hydroxyethylpiperazine-N'-2-ethanesulfonic acid (HEPES; H-3375), soybean trypsin inhibitor (T-9003 Type IS), poly-D-lysine hydrobromide (P-7886, $M_r$ 30,000–70,000), human transferrin (T-2252), bovine insulin (I-5500), progesterone (P-0130), putrescine dihydrochloride (P-7505), and phenylmethylsulfonyl fluoride (PMSF; P-7626), deoxyribonuclease I (D-4513), sucrose (S-9378 Grade 1), and Percoll (P-1655) from Sigma, St. Louis, MO; sodium selenite (spectrographically pure) from Johnson Matthey Chemical, London; biotin (2031) from Calbiochem-Behring, San Diego, Calif.; sodium citrate (SX0445-1) from MCB, Cincinnati, Ohio; ultra pure urea (821527) from ICN, Cleveland, Ohio; Falcon sterile 100 ml plastic cups, polypropylene centrifuge tubes, and tissue culture plastic ware from Becton Dickinson, Oxnard, Calif.; Lab-Tek tissue culture chamber slides from Miles Laboratories, Naperville, Ill.; 5.5" scissors (6812), 4" dissecting scissors (5882), 4" curved forceps (5135), and 4" dissecting forceps (5095) from Roboz Surgical, Washington, DC; glass pestle (1985-11516), metal tissue sieve (1985-85000), 380 $\mu$m (#40) metal mesh, and 140 $\mu$m (#100) metal mesh from Bellco, Vineland, N.J.; 25 mm (XXIO02530) and 47 mm (XX1004730) glass microanalysis filter holders from Millipore, Bedford, Mass.: 20 $\mu$m (#460), 60 $\mu$m (#250), and 210 $\mu$m (#70) nylon mesh from Tetko, Elmsford, N.Y.; 10 ml Oak Ridge-style polycarbonate tubes (2611-B18) from Thomas Scientific, Swedesboro, N.J.

Antibodies were obtained as follows: mouse antigalactocerebroside hybridoma from B. Ranscht (MIT, Cambridge, Mass.); A2B5 hybridoma from M. Nirenberg (NIH, Bethesda, Md.); Thy 1.1 hybridoma from R. Pruss (Merrell-Dow, Cincinnati, Ohio); monoclonal anti-GFAP and anti-200-kilodalton.(kd) neurofilament (NF) from Labsystems, Chicago, Ill.; monoclonal anti-68-kd NF from Amersham, Arlington Heights, Ill.; monoclonal anti-myelin basic protein from Hybritech, San Diego, Calif.; fluorescein- and rhodamine-conjugated goat anti-mouse IgG (heavy and light chain-specific), rhodamine-conjugated goat anti-rabbit IgG, whole mouse and goat sera, and rabbit complement from Cappel Laboratories, Malvern, Pa.; anti-MAC-1 in ascites fluid and fluorescein-conjugated goat anti-rat IgG from G. Klimpel (Univ. of Texas, Galveston, Tex.); rabbit anti-human fibronectin from Bethesda Research Laboratories, Gaithersburg, Md.; $^3$H-[methyl]thymidine (specific activity 30 Ci/mmol) from Schwarz-Mann, Spring Valley, NY. Unless otherwise specified reagents are from Sigma, St. Louis, Miss..

Cell Lines. B104 is a rat CNS neuroblastoma and was obtained from D. Schubert (Salk Institute, La Jolla, Calif.). This cell line is available from the ATCC under accession #CLR 10187. This cell line was deposited with the American Type Culture Collection, 12301 Parklawn Drive, Rockville, Md. 20852 on Jul. 26, 1989. Other cell lines used in this study were CO-13-7 calf brain oligodendrocyte x C6 rat CNS glioma somatic cell hybrid form F. McMorris (Wistar Institute, Philadelphia, Pa.); U251 MGsp human CNS glioma from D. Bigner (Duke University, Durham, N.C.); C62B rat CNS glioma from J. de Vellis (University of California, Los Angeles, Calif.); 2LI human PNS neuroblastoma clone isolated in this laboratory from the LA-N-1 cell line provided by R. Seeger (University of California, Los Angeles, Calif.).

Water. High quality water is essential for culture medium and other reagents when serum-free methods are used. The following low maintenance water purification system is recommended: deionized water input, prefilter, carbon cartridge, two ion-exchange cartridges, pyrogen removal cartridge, and a final 0.22 $\mu$m filter unit in series. Purified water should have a resistance of 10–18 megohm-cm. alternatively, triple-distilled water is suitable.

Basal Medium. DME is used alone or mixed 1:1 with F12 medium. HEPES buffering agent is added to give a final concentration of 15 mM, and after mixing the pH is adjusted to 7.3. Finally, 1.2 g/l sodium bicarbonate is added, medium is sterile-filtered (0.22 $\mu$m), and stored 6 weeks or less in the dark at 4 degrees C in aliquots.

Serum-free Media. All medium supplements are sterile-filtered and stored at $-20°$ C. unless otherwise noted. Stock solutions: 10 mg/ml transferrin in HBSS+; 2.5 mg/ml insulin in 0.01 N HCl stored at 4° C. only for six weeks or less; 0.5 mM primary selenite stock in water and 15 $\mu$m secondary stock in HBSS+; 1 mM primary progesterone stock in ethanol stored at 4° C. and 10 um secondary stock in HBSS+; 50 mM putrescine in HBSS+; and 10 $\mu$g/ml biotin in HBSS+.

When preparing and handling the following serum-free media, plastic pipets and containers should be used to minimize protein adsorption. 01 Medium: 5 $\mu$g/ml insulin (or 100 ng/ml IGF I), 50 $\mu$g/ml transferrin, 30 nM selenite, and 10 ng/ml biotin in DME. 03 medium: 15 $\mu$g/ml insulin, 1 $\mu$g/ml transferrin, 30 nM sodium selenite, and 10 ng/ml biotin in DME or a 1:1 mixture of DME and F12. N4 medium: 1 $\mu$g/ml transferrin, 5 $\mu$g/ml insulin, 100 $\mu$M putrescine, 20 nM progesterone, and 30 nM selenite in a 1:1 mixture of DME and F12. 01, 03 and N4 medium are prepared fresh before use, as some loss of growth-promotion is observed when medium is stored at 4° C. for 1 week. Culture medium pH should always be 7.3 on initial contact with cells. It is advisable to equilibrate culture vessels containing medium in the CO$_2$ incubator before adding cells. Culture medium rapidly becomes alkalinized from exposure to air, especially in the laminar flow hood. For best results, cultured cells should spend minimal time in the sterile hood or in microscope observation.

Substratum Modifications. When using serum-free medium, all culture surfaces should be modified by precoating with at least 2 $\mu$g/cm$^2$ poly-D-lysine, followed by the addition of 1 $\mu$g/cm$^2$ affinity-purified human fibronectin (see below) for an optimal response to the soluble growth-promoting factors. Surfaces are completely covered for 5 minutes with a 0.05 mg/ml sterile solution of polylysine in water, followed by a sterile water wash; precoated vessels may be stored before use for several hours in a hydrated form (Bottenstein and Sato, 1980). The water wash is aspirated, serum-free medium is added, fibronectin is added individually to vessels with swirling to ensure even distribution of this highly adhesive glycoprotein, and finally, cells are added.

Purification of Fibronectin. Human fibronectin is purified (>98% by SDS gel electrophoresis) from plasma at room temperature by gelatin-Sepharose chromatography (Bottenstein, 1984). Briefly, 0.45 μm filtered plasma is applied to the column. After washing out unbound material with phosphate buffered saline containing 0.01 M sodium citrate (PBS/citrate; pH 7.2), fibronectin is eluted with 0.05 M Tris-HCl buffer (pH 7.4) containing 4 M urea. Fractions are collected in polypropylene tubes, and protein content is determined. Peak fractions are combined to obtain 0.25-1 mg/ml and are dialyzed at 4° C. against PBS/citrate containing 1 M urea. About 10-30 mg of fibronectin can be isolated from 250 ml of human plasma. The protein concentration of the dialyzed solution is determined, and aliquots are made and stored at 4° C.; activity has been retained for as long as 4 months. Division of a neuronal cell line is used to bioassay the fibronectin; usually 0.25-1.5 μg/cm$^2$ is optimal depending on the batch used. Commercial sources (Sigma, Bethesda Research Labs, and others) of fibronectin may require higher amounts for optimal activity.

Preparation of B104 Cell Conditioned Medium. Neural progenitor cell regulatory factor is found in conditioned medium produced by clonal B104 CNS neuroblastoma cells. Stock cultures of B104 cells are maintained in logarithmic phase in a 1:1 mixture of DME and F12 supplemented with 5% horse serum and 5% fetal bovine serum. After a wash with Hank's balanced salt solution (HBSS), cells are detached with 0.05% trypsin/0.5 mM EDTA in phosphate buffered saline (PBS; pH 7.0), 0.1% soybean trypsin inhibitor in HBSS+ is added, cells are centrifuged for 2 min. in a tabletop centrifuge at lowest speed, the cell pellet is resuspended in N4 medium, and 10 cells/cm$^2$ are plated into 75 cm$^2$ tissue culture flasks with polylysine and fibronectin-modified surfaces. Four to five days later the conditioned medium is removed sterilely, 1 μg/ml of the protease inhibitor PMSF in ethanol is added, centrifuged at 3500 rpm for 15 min. at 4° C. to remove nonadherent cells, and aliquots are stored at −70° C.

Production of Large Volumes of B104 Conditioned Medium by Culture With Microcarrier Beads. A preferred method for preparation of conditioned medium from the B104 cell line comprises culture on microcarrier beads. With this method, either a 100- or 500-ml microcarrier flask is used with 0.3 g or 1.5 g (5.5×10$^3$ cm$^2$ surface area/g) of Cytodex 2 beads (Pharmacia), respectively. B104 cells are plated at 2.65×10$^4$ cells/cm$^2$ in serum-free N4 medium (modified N2 medium $^{(Bottenstein\ and\ Sato,\ 1979)}$ consisting of 1 μg/ml human transferrin, 5 μg/ml bovine insulin, 100 μM putrescine dihydrochloride, 20 nM progesterone, and 30 nM sodium selenite in a 1:1 mixture of Ham's F12 medium and DME). Affinity-purified human fibronectin$^{(Bottenstenstein\ and\ Sato\ 1980)}$ (0.06 μg/cm$^2$) is added before plating. In the experiments described below, after 4 days, the first collection of conditioned medium was made (crude CM; 24-36 μg protein/ml). This CM was used for experiments with neonatal rat brain cells grown in various dilution (8-66%; v/v). After collection, fresh N4 medium was added, and three more collections were made at 4-day intervals. This material was pooled and concentrated about 10-fold in an Amicon hollow fiber concentrator (M, cutoff 5 or 10 kd), with dialysis against an 100-fold excess of 5 mM sodium phosphate buffer containing 50 mM sodium chloride, pH 7.4. It is estimated that at least 18-30 μg/ml of CM protein (75-83%) is derived from the B104 cells, since only 6 μg protein/ml is added to N4 medium initially. Protein concentrations were assayed by a modification of Sedmark and Grossberg (1977) using egg white lysozyme as a standard.

Dissociated Neonatal Rat Brain Cells. Sprague-Dawley newborn rat pups (1-3 days postnatal) are used. A maximum of about 6 pups/person are processed to maximize the yield of cells/pup. All dissecting instruments and equipment are autoclaved prior to the dissociation procedure, which is performed sterilely in a laminar flow hood. Sterile 100 ml plastic cups with metal sieves (380 μm and 140 μm) to collect the first two filtrates are set up in the hood. A glass filter apparatus with a 20 μm nylon mesh installed is clamped onto a stand, and a 50 ml polypropylene centrifuge tube is placed underneath to catch the final filtrate. Dissociation medium is prepared: DME supplemented with 10% calf serum, 50 μg/ml penicillin, 50 μg/ml streptomycin, 10 μg/ml neomycin, and 50 μg/ml gentamicin; 100 ml is sufficient for one litter of pups (2 simultaneous dissociations).

Each pup is held by its muzzle and rinsed with 70% ethanol from a spray bottle and then quickly decapitated using large scissors. The severed head is placed on a gauze square and held firmly at the jaws. The scalp is cut with small scissors along the midline from the neck as far anteriorly as possible. The scalp is retracted with the fingers, being careful not to contaminate underlying tissue. The cartilaginous skull is similarly incised starting at the foramen magnum. The meninges between the skull and the dorsal brain surface are separated by insertion of the point of the blunt forceps and a gentle back-and-forth movement. Each side of the skull is pulled away laterally with forceps to expose the brain surface. A spatula severs the olfactory tract and cranial nerves, and the whole brain is lifted from the base of the skull and placed in a small petri dish with enough dissociation medium to cover the brain. After each use of a dissecting instrument, it is dipped in ethanol and allowed to dry while resting tip up on a petri dish.

After all the brains are collected, they are trimmed of residual meningeal tissue. Each brain is held with fine forceps and the sheets of fibrous tissue, which are closely adherent to the brain surface and contain prominent blood vessels, are pulled free with blunt forceps. If a specific part of the brain is to be used, e.g., cerebellum or cerebral cortex, it can be dissected free at this time. After the meninges are removed, the brains are transferred to a 60 mm petri dish containing 7 ml of dissociation medium. The brain is then minced with fine scissors for 4 min. to produce 1-3 mm fragments. The 380 μm metal mesh is wetted with 1 ml of dissociation medium and is spread evenly with a glass pestle. The brain fragments are swirled to suspend them, poured into the center of the mesh, and pressed through with gentle vertical motions of the glass pestle for 2 min. The fragments are wetted every 30 seconds with 0.5 ml of dissociation medium. The mesh is rinsed from above with 2 ml of dissociation medium and from the bottom by pipetting several ml of the filtered cell suspension onto the underside of the mesh. The finer 140 μm mesh is wetted with 1 ml of dissociation medium and is spread evenly with the plunger of a 5 ml disposable syringe. The first filtrate is added to the second mesh and stirred with the plunger. In addition, gentle vertical motion of the plunger for 2 min. pushes the cells through the mesh. Small volumes of dissociation medium are frequently applied to keep the cells hydrated. The second mesh is washed as described above. The 20 μm nylon mesh in the filter apparatus is wetted with 1 ml of dissociation medium and checked for leaks. The cell suspension is then poured into the filter apparatus and stirred gently and continuously with a glass rod. The single cell filtrate is collected for up to 15 min; flow rate averages about 1 ml/min for 15 min. if continuously stirred. Gentle, brief agitation of the filter apparatus increases the flow rate slightly. The last few ml usually do not pass through because the flow rate slows markedly at the end.

The final filtrate is centrifuged at low speed (100 ×g) in a table-top centrifuge for 3 min., and the supernatant is discarded by aspiration. The cell pellet is resuspended in 03 medium (0.5 ml/brain) with penicillin/streptomycin/neomycin but no gentamicin. A 1:10 dilution of the cell suspension is counted in a hemocytometer. The typical yield is $25-30 \times 10^6$ cells/brain. Optimal plating density with this method is $5 \times 10^5$ cells/cm$^2$; each culture vessel is rocked back and forth several times (avoiding vortexing) to evenly distribute the cells. Cultures are kept in the sterile hood a minimal time to avoid alkaline shifts in pH. If many culture vessels are to be inoculated, it is important to gently agitate the concentrated cell suspension frequently to maintain the cells in suspension and inhibit aggregation. Attachment of cells occurs rapidly in serum-free medium, but it is best not to disturb the cultures for at least 24 hr. A plating efficiency of about 5-10% can be expected. Media are first changed after 4 days and at 3-5 day intervals thereafter depending on the pH (more often if the medium becomes acidic). Antibiotics are only present in the initial plating medium.

Characterization of neonatal Cultures in Serum-Free Medium. It is important to include a control condition for comparison to experimental treatments. Immunostaining for cell-type specific antigens is a preferred method for identifying the cells, and is described more completely below. Typically, after 4 days in serum-free 03 medium, the cultures contain about 70% type 1 astrocytes, 15% oligodendrocytes, 2% 0-2A progenitor cells, 2% type 2 astrocytes, and 7% microglia by immunostaining criteria. Less than 1% of cells are neurofilament-positive, <2% are Thy-1 antigen-positive, and total cell density is typically 300 cells/mm$^2$. After 1 week or longer most cellular debris disappears due to the action of phagocytic cells. Since most bipotential glial progenitors differentiate rapidly into oligodendrocytes in serum-free medium, this system is useful for studying growth factors for glial progenitors and immature oligodendrocytes, as well as for analysis of differentiated oligodendrocytes. These cultures can be maintained for several months in 01 or 03 medium.

Figure 1B:
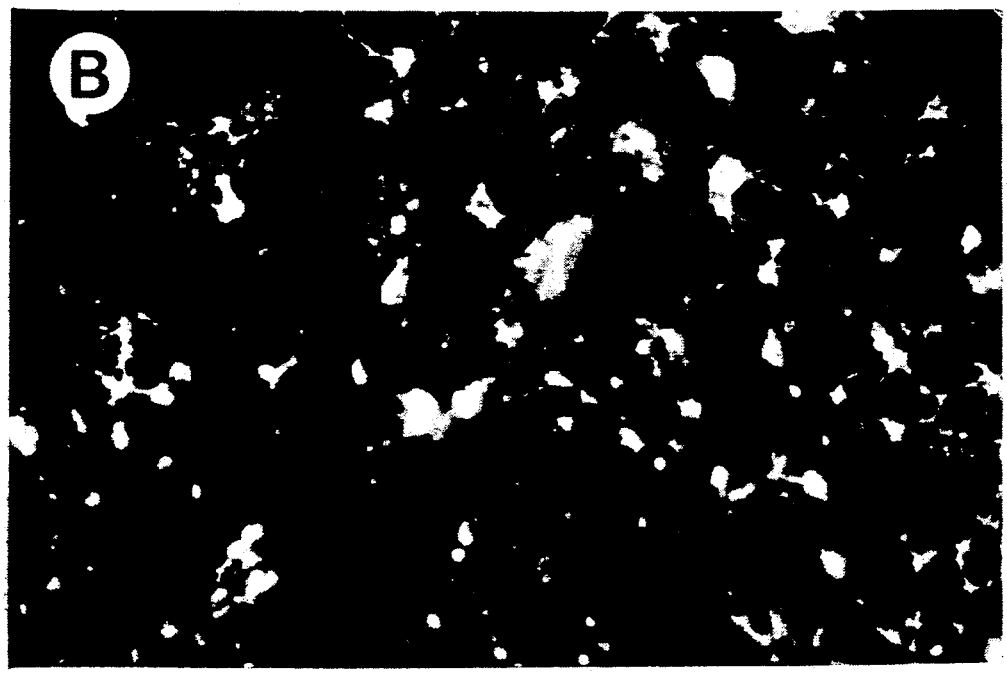

Treatment with B104 Conditioned Medium. To enhance the yield of 0-2A lineage cells, neonatal rat brain cultures are treated with conditioned medium (CM) derived from B104 CNS neuroblastoma cells. The combined use of 03 medium and B104 CM is both simple and reliable. The results shown generally were obtained with 8-12 μg CM protein/ml, which represents about 33% conditioned medium/67% 03 medium (v/v). Control cultures contain an equivalent dilution with unconditioned N4 medium. It is important for the CM to be present from the time of plating, since progenitor cell differentiation will rapidly occur otherwise. After 4 days in vitro, 51% type 1 astrocytes, 23% 0-2A progenitors, 15% oligodendrocytes, 6% microglia, and 3% type 2 astrocytes are present; total cell density is about 400 cells/mm$^2$. By 8 days in vitro, 53% type 1 astrocytes, 22% oligodendrocytes, 15% 0-2A progenitors, 6% microglia, and 3% type 2 astrocytes are present; total cell density is about 500-600 cells/mm$^2$ (Table I). The increase in 0-2A progenitors is 12 to 15-fold over control at both times, and oligodendrocytes are increased about 4-fold over control at 8 days in vitro. FIG. 1 shows the multipolar process-bearing morphology and expression of the oligodendrocyte-specific galactocerebroside antigen in these cultures at 9 days in vitro. Note the extensive network of oligodendrocyte processes. After 3 weeks in culture, the activity of the myelin-specific enzyme 2',3'-cyclic nucleotide 3'-phosphodiesterase is increased 12-fold over the 03 medium control.

TABLE I

Cellular phenotypes in neonatal rat brain cultures at 4 and 8 days in vitro (DIV) in the absence or presence of 33% B104 conditioned medium.

| Cell Type | Cells/mm$^1$ ± SEM (% of total cells) | | | |
|---|---|---|---|---|
| | 4 DIV | | 8 DIV | |
| | Control | Treated | Control | Treated |
| O-2A lineage | | | | |
| Progenitors | 6 ± 1 (2) | 87 ± 7$^c$ (23) | 7 ± 3 (2) | 83 ± 9$^c$ (15) |
| Type 2 Astrocytes | 7 ± 1 (1) | 11 ± 3 (3) | 4 ± 1 (1) | 14 ± 1$^c$ (3) |
| Early Oligodendrocytes | 31 ± 6 (10) | 47 ± 7 (13) | 13 ± 3$^d$ (4) | 80 ± 10$^{c,f}$ (14) |
| Late Oligodendrocytes | 13 ± 1 (4) | 7 ± 3 (2) | 24 ± 4 (7) | 41 ± 7$^{a,f}$ (7) |
| Total Oligodendrocytes | 44 ± 7 (15) | 54 ± 6 (15) | 37 ± 6 (10) | 121 ± 10$^{c,f}$ (22) |
| Total O-2A lineage | 57 ± 6 (19) | 152 ± 3$^c$ (41) | 48 ± 4 (13) | 218 ± 6$^{c,f}$ (39) |
| Non-O-2A lineage | | | | |
| Type 1 Astrocytes | 217 ± 9 (72) | 190 ± 27 (51) | 266 ± 30 (74) | 296 ± 33$^d$ (53) |
| Microglia | 21 ± 3 (7) | 24 ± 1 (6) | 37 ± 3$^e$ (10) | 34 ± 3$^d$ (53) |
| Other | 6 ± 1 (1) | 6 ± 1 (2) | 7 ± 1 (2) | 9 ± 3 (2) |

TABLE I-continued
Cellular phenotypes in neonatal rat brain cultures at 4 and 8 days in vitro (DIV) in the absence or presence of 33% B104 conditioned medium.

| | Cells/mm$^1$ ± SEM (% of total cells) | | | |
|---|---|---|---|---|
| | 4 DIV | | 8 DIV | |
| Cell Type | Control | Treated | Control | Treated |
| Total cells | 301 (100) | 372 (100) | 358 (100) | 557 (100) |

Table I Legend:
Dissociated neonatal rat brain cells are treated with 33% unconditioned N4 medium/67% O3 medium (control) or 33% B104 conditioned medium (CM; 12 μg/ml)/67% O3 medium for 4 or 8 DIV. Cellular phenotypes were assessed by indirect immunofluorescence. Total cells identified by immunostain were not significantly different from those obtained by counting under phase-contrast (Student's t test). The other category consists of Thy1.1-positive cells, which can be fibroblasts or neurons. Neurons identified as either 68-kd or 200-kd neurofilament-positive are 0.2-1.0% in all conditions, and their numbers are not significantly different between CM-treated and control cultures. Fibronectin-positive cells, which can be fibroblasts, meningeal cells, ependymal cells, or some astrocytes represent 2-5% of cells in either condition. Cells with motile cilia (ependymal cells) are rarely observed. Statistical significance was tested by Fisher's Least Significant Difference. Control vs. treated conditions:
$^a p < 0.05$,
$^b p < 0.025$,
$^c p < 0.004$;
4 DIV vs. 8 DIV for the same condition:
$^d p < 0.05$,
$^e p < 0.025$,
$^f p < 0.004$.

Enhanced Differentiation into Oligodendrocytes or Induction of Type 2 Astrocytes. To selectively enhance differentiation of O-2A progenitor cells into oligodendrocytes, B104 conditioned medium is removed at 4 days in vitro and replaced with serum-free O3 medium. Three days later, oligodendrocytes are increased 3-fold, representing a 5-fold increase compared to cells in O3 medium for 7 days, a condition which already favors oligodendrocyte development. The resulting cultures are about 33% oligodendrocytes. Alternatively, to selectively induce differentiation into type 2 astrocytes, B104 conditioned medium is removed at 4 days in vitro and replaced by O3 medium with 10% fetal bovine serum. Three days later, type 2 astrocytes are increased 12-fold, representing a 32-fold increase compared to cells in O3 medium for 7 days. Type 1 astrocytes also proliferate vigorously in serum-containing medium. These cultures contain about 18% type 2 astrocytes.

Percoll Density Gradient Procedure. Most of the cellular debris and erythrocytes present in the cell suspension at the time of initial plating can be removed by centrifugation in a Percoll gradient before plating. This is recommended when cultures are to be analyzed within the first week in vitro. A 10-ml Oak Ridge-style polycarbonate tube is rinsed with 70% ethanol and allowed to dry in the sterile hood. A 1.25 M sucrose stock solution in water is made and filter-sterilized. An 80% Percoll stock solution is made by adding 2 ml of sucrose stock to 8 ml of sterile Percoll. First, $10^8$ dissociated neonatal rat brain cells are added to the polycarbonate tube, followed by 2.8 ml of 80% Percoll, and finally additional dissociation medium to give an evenly dispersed mixture of cells in a final volume of 9.5 ml (23% Percoll/75 mM sucrose). Another tube is made with the same components but no cells. The tubes are balanced and spun at 21,600 rpm (30,000 ×g) for 45 min. in a Ti50 rotor in a Beckman L8M ultracentrifuge at 4° C. Several layers result: a thin layer of debris on top; a thick, opaque layer of debris; a cloudy layer of debris; a clear, cell-containing layer; a thin, erythrocyte-containing layer; and an amber bottom layer of Percoll. The upper layers of debris are discarded by aspiration. The clear, intermediate cell layer (2-3 ml) above the erythrocyte layer is carefully transferred to a 15 ml centrifuge tube using a sterile pasteur pipet. The cells are washed first by adding 12 ml of dissociation medium and spinning at 190 ×g in a tale-top centrifuge for 10 minutes, washed again with 5 ml HBSS+, and resuspended in 1 ml of O3 medium. An aliquot is counted after a 1:10 dilution, and cells are plated at $1.3-2.5 \times 10^5/cm^2$. Only about 10% of the cells applied to the gradients are recovered. However, since the plating efficiency is about 25% compared to 5-10% in the standard dissociation method, 2- to 4-fold less Percoll gradient-processed cells are plated.

Figure 2:
FIG. 2: Percoll gradient-processed neonatal rat brain cells at 3 days in vitro. Cells were plated in 03 medium with 33% B104 conditioned medium on polylysine- and fibronectin-modified culture surfaces. Bar = 50 microns.

A typical field of mainly bipolar O-2A progenitors is shown in FIG. 2 after 3 days in vitro. Cells were plated into 33% B104 CM/67% O3 medium. This method produces cultures that are significantly cleaned up and have less background in subsequent immunostaining procedures.

Enrichment of O-2A Lineage Cells. The inventor has also developed a method to decrease the percentage of non-O-2A lineage cells in the cultures. Enriched secondary cultures are derived from primary cultures of dissociated neonatal rat brain cells in serum-containing medium by separating the superficial, process-bearing cells from the underlying bed layer of primarily type 1 astrocytes and microglia (Bottenstein, 1986). Using the standard dissociation procedure above, $5 \times 10^5$ cells/cm$^2$ are plated in 75-CM$^2$ tissue culture flasks in DME supplemented with 15% calf serum on polylysine-coated surfaces. At 7-13 days in vitro, the cultures are washed once with HBSS$^-$, incubated in the same solution for 4 minutes, and vigorously shaken for 5 seconds at the end of every minute. The cell-laden supernatants are replated at $2 \times 10^2$ cells/cm$^2$ in serum-containing medium or onto polylysine and fibronectin-modified surface in O3 medium. A plating efficiency of 80-100% can be expected.

Figure 3A:
FIG. 3A-C: Phase contrast micrographs of cells maintained in DME supplemented with 10% calf serum. (A) mixed culture after 13 days in culture; (B) isolated process-bearing cells obtained from (A) and shown 2 days later, (C) remaining bed layer of primarily type 1 astrocytes obtained from (A) and shown 2 days later. Bar = 100 microns.
Figure 3B:
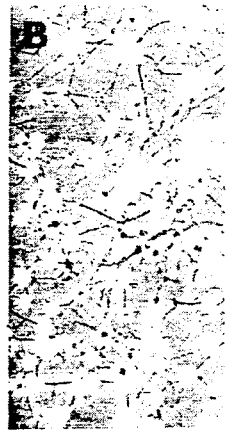
Figure 3C:
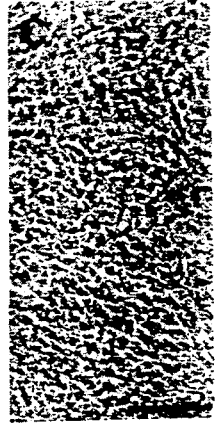

FIG. 3 shows cells prior to the isolation procedure (FIG. 3A). Excellent separation of the process-bearing cells (FIG. 3B) from the bed layer (FIG. 3C) is evident in these serum-containing cultures. If serum-free culture is used after the isolation, secondary cultures after 1 day in O3 medium contain: 24-30% GFAP-positive cells (mostly type 1 astrocytes), a 2-3 fold decrease in percentage compared to primary cultures after 4 days in vitro; 26% galactocerebroside-positive oligodendrocytes, a 2-fold increase compared to primary cultures after 4 days in vitro; and 54% A2B5-positive cells (immature oligodendrocytes and O-2A progenitors), a 4-fold increase compared to primary cultures after 4 days in vitro. The ratio of GFA-positive to A2B5-positive cells in decreased 8 to 12-fold, indicating substantially fewer contaminating cells. The 0-2A progenitors in this enriched preparation are equally responsive to the growth factors in B104 conditioned medium as are the original cultures. Thus, the contaminating type 1 astrocytes probably play no role in the growth factor action.

B. Methods For Phenotypic Analysis of Cultured Glial Cells and Their Progenitors Immunostaining. An indirect immunofluorescence method can be used to identify surface and intracellular antigens for the purpose of classifying glial and other cells. The following describes one protocol that has been successfully used by the present inventor. Hybridoma cells are grown in a 100 mm petri dish ($5 \times 10^6$ inoculum) for four days in serum-free medium (2.5 μg/ml bovine insulin, 25 nM sodium selenite, 35 μg/ml human transferrin, and 20 μM ethanolamine in 1:1 DME:Ham's F12 medium). Hybridoma supernatants (SNs) are concentrated either in an Amicon stirred-cell ultrafiltration apparatus (100 kd cutoff) or with an Amicon disposable macrosolute concentrator (15 kd cutoff). Concentrated A2B5 hybridoma SN (25-fold) is used at a 1:6 dilution; galactocerebroside (GalC) hybridoma SN is used at 1:4 dilution without prior concentration; concentrated Thy1.1 hybridoma SN (10-fold) is used at a 1:2 dilution. Monoclonal anti-GFAP in ascites fluid is diluted 1:50–100. Monoclonal anti-myelin basic protein in ascites fluid is diluted 1:100. Both goat anti-mouse and anti-rabbit IgG-rhodamine and -fluorescein conjugates were used at 1:80 dilution. Anti-fibronectin, anti-MAC-1, and anti-rat IgG-fluorescein were diluted in PBS; other antibodies were diluted with 5% goat serum, 5% calf serum, 45% DME, 45% phosphate-buffered saline.

Cultures stained for A2B5 were fixed with 3.7% p-formaldehyde in PBS, followed by three washes (1 ml for 35 mm dishes, 09.5 ml for chambers) in HBSS. The antibody was applied for 30 min., and cultures were washed as above. Goat anti-mouse IgG-rhodamine conjugate was then applied for 30 min. and then washed as above. Even though the A2B5 antibodies are IgM, the antisera also react with mouse light chains. Equivalent staining is obtained using anti-mouse IgM, μ-chain-specific. The culture was then post-fixed with 3.7% p-formaldehyde in PBS for 20 min. and then washed as above. The post-fixation step prevented loss of antibody, if a double stain was subsequently performed. Application of a saturating amount of the rhodamine-labeled antibody insured that no cross-reaction would occur in a subsequent stain using anti-mouse IgG-fluorescein conjugate. If a second immunostain was against an intracellular antigen, e.g. GFAP, MBP or NF, the culture was treated for 10 min. with 95% ethanol:5% acetic acid at $-20°$ C. to permeabilize the membrane and then washed rapidly four times in cold HBSS. If the second stain was to reveal a different surface antigen, e.g. GalC, this permeabilization was not performed. The above staining procedure was then repeated with the second antibody followed by an appropriate fluorescein-conjugated anti-mouse IgG antibody. A2B5 antibody was always visualized with anti-mouse IgG-rhodamine conjugates and anti-GalC, anti-GFAP, and anti-NF antibodies with anti-mouse IgG-fluorescein conjugates.

Single stains for Thy-1, fibronectin, and MAC-1 were carried out on unfixed cultures because of the sensitivity of these peptide antigens to p-formaldehyde. Microglia were identified using anti-MAC-1 (from M1/70 clone ascites fluid 1:100) and anti-rat IgG-fluorescein (1:50) or with mouse serum (1:50) and goat anti-mouse IgG-rhodamine (1:50; these combinations appeared to identify the same population, which was also morphologically consistent with microglia.) Staining with Thy1.1 antibody and anti-mouse IgG-rhodamine (1:80) was used to estimate non-glial types present in primary cultures (fibroblasts and neurons). Rabbit anti-fibronectin and goat anti-rabbit IgG-rhodamine were used to reveal fibronectin, and goat anti-rabbit IgG-rhodamine was used to reveal fibronectin-positive cells, which were readily distinguishable from the background substratum-bound fibronectin. Both anti-68-kd NF and anti-200-kd NF were used to demonstrate neuronal cell types.

Glial subtypes of the type 1 astrocyte and the oligodendrocyte/type 2 astrocyte lineages were determined from double stains for A2B5/GalC and A2B5/GFAP. Cells were categorized as follows: A2B5-negative/GalC-positive, late oligodendrocyte; A2B5-positive/GalC-positive., early oligodendrocyte; A2B5-negative/GFAP-positive, type 1 astrocyte; A2B5-positive/GFAP-positive, type 2 astrocyte. Progenitor cells were determined by taking the difference between the number of A2B5-positive/GalC-negative and A2B5-positive/GFAP-positive cells to get the number of A2B5-positive/GalC-negative/GFAP-negative cells. The 35-mm dishes were partitioned with a line of silicone vacuum grease (Dow-Corning), and each half was double-immunostained for either A2B5/GalC or A2B5/GFAP. Chamber slides had most chambers stained for A2B5/GalC and some for A2B5/GFAP. Cells were scored as positively stained when characteristic staining patterns (membrane for GalC and A2B5, fibrillary for GFAP) were present at intensities greater than nonspecific staining. For anti-GalC staining, evaluation of weak staining was done by comparison to the more morphologically mature phenotypes present in the culture which exhibited strong anti-GalC-reactivity.

Cell numbers were expressed either by cells/mm$^2$ or as the fold-change relative to control cell density. Most cultures were evaluated at $400\times$ magnification, and for most experiments, at least 200 cells per culture were evaluated. Controls conducted with no primary antibody, mouse serum (on fixed cultures), or irrelevant antibodies showed no specific staining patterns.

Complement lysis. Concentrated A2B5 (25-fold) or GalC (5-fold) hybridoma supernatant was added to cultures (4 DIV) grown in the present of 33% CM; final concentrations were 40 μg/ml for GalC. After 30 minutes at $37°$ C., each culture was washed twice with HBSS. Then 0.8 ml of rabbit complement in DME (1:10) was added and incubated 45 min. at $37°$ C. Cultures were then washed once with DME containing 10% calf serum, twice with HBSS, and finally fresh 03 medium with 33% CM was added. Cultures were fixed 24 h. or 4 days after the complement treatment. Numbers of A2B5-and GalC-positive cells were evaluated by indirect immunofluorescence as above. There were no significant differences between mean densities of either A2B5-positive or GalC-positive cells in CM-treated cultures with no complement versus those with complement by Student's t test at both times studied. Densities of A2B5-and GalC-positive cells were expressed as cells/mm$^2$, but for further statistical analyses the fold-change in density relative to a paired control (no complement, CM-treatment, or antibody) was determined. This reduced inter-experimental variability.

Autoradiography combined with immunostaining. Cells grown in chamber slides were exposed to $^3$H-thymidine (1 μCi/ml, 30 Ci/mmol) for either 24 or 6 h. prior to fixation. After immunostaining, slides were coated with Kodak NTB2 photographic emulsion:distilled water (1:1) and exposed 6 days at 4° C. with a desiccant prior to development in Kodak D19 and mounting. Cells showing ten grains or more over the nucleus were scored as thymidine-labeled, and the labeling indices (percent labeled cells) for populations of immunostained cells (GalC, A2B5, or GFAP) were determined. Evaluation was carried out at 400×magnification using a combination phase contrastepifluorescence objective.

Enzyme Assays. For enzyme assays used in characterization, cells are grown in 25-cm$^2$ flasks, washed two times with PBS at 4° C., harvested with a rubber policeman at 4° C. in high-quality water or 0.01 M sodium phosphate buffer (pH 7.1) and stored at $-70°$ C.

Assay for 2',3'-cyclic nucleotide 3'-phosphodiesterase. Activity is measured by a modification of the method of Prohaska et al., 1973). Samples harvested in water are thawed, sonicated on ice, and 18.5 μl are aliquoted into acid-washed Pyrex tubes. The enzyme is activated with 18.5 μl of 0.1% saponin in 20 mM Tris-HCl buffer (pH 7.5) on ice for 10 min, followed by addition of 37 μl of 15 mM 2',3'-cyclic AMP in 0.1 M Tris-maleate buffer (pH 6.2) for 20 min at 30° C. in a shaking water bath and termination of the reaction by boiling for 2 min. Then 37 μl of 0.3 M Tris-HCl buffer (pH 9) with 21 mM MgCl$_2$ and 7.4 units of Escherichia coli alkaline phosphatase/ml is added to samples in a shaking water bath for 20 min. at 37° C. Finally, 444 μl of 1.5% ammonium molybdate in 0.5 M sulfuric acid is added to the reaction mixture in a fume hood, and the yellow phosphomolybdic acid complex is extracted with 444 μl of isobutanol/benzene (1:1), followed by vortexing for 20 sec and centrifugation at 2,200 rpm for 5 min. 2'-AMP standards are processed as above beginning with the phosphatase step. The upper-layer absorbance is read at 405 nm and compared to standards. Relative enzyme activity is expressed as nmoles of 2'-AMP/min/cm$^2$.

Assay for glutamine synthetase. Activity is measured by a modification of the method of Kirk (1965). Samples harvested in phosphate buffer are thawed, sonicated on ice, and 350 μl of freshly made 0.1 M acetate buffer (pH 5.4) containing 120 μmol L-glutamine, 5 μmol NaH$_2$PO$_4$, and 0.05 μmol ATP is added for 10 min at 37° C. The reaction is started by adding 150 μl of 0.1 M acetate buffer (pH 5.4) containing 30 μmol hydroxylamine and 5 μmol MnCl$_2$. After 20 min, 750 μl of 5% trichloroacetic acid/1.6% FeCl$_3$ in 0.33 N HCl is added to each tube. After vortexing, absorbance is read at 490 nm and compared to standards. Relative enzyme activity is expressed as nmoles of gamma-glutamohydroxamate/min/cm$^2$.

Protein assay. The Sedmark and Grossberg (1977) protein assay was used with egg white lysozyme as the standard. It was modified to a microassay using 96-well microplates and triplicate samples.

C. Further Biological Characterization of Neural Progenitor Regulatory Factor

Effect of Conditioned Media From Various Cell Lines on Neonatal Rat Brain Cells. The present inventors screened conditioned media from several cell lines of neuronal or glial phenotype on dissociated neonatal rat brain cells. Phase contrast micrographs of 9-day-old cultures maintained in the presence of 50% conditioned medium and 50% 03 medium are shown in FIG. 4. Oligodendrocytes can be identified morphologically as the small (cell diameter 8-12 μm), phase-dark process-bearing cells. The relative numbers of morphologically identified oligodendrocytes in these cultures are the following: conditioned medium from B104 rat CNS neuroblastoma >>CO-13-7 calf brain oligodendrocyte/C6 rat CNS glioma hybrid >U251 MGsp human CNS glioma >C62B rat CNS glioma >RN22 rat PNS schwannoma >>2L1 human PNS neuroblastoma =N1E-115 mouse PNS neuroblastoma cells. Immunostaining for the oligodendrocyte marker galactocerebroside (GalC; Raff et al., 1978) confirmed this ranking. Thus, it is clear from these initial results that conditioned media from CNS-derived cells increases the number of oligodendrocytes to a greater extent than that from PNS-derived cells, and CNS neuron-derived conditioned medium has a much greater effect than any of the glia-derived or PNS neuron-derived conditioned media. Cell-free extracellular matrices prepared from these same cell lines had no oligodendrocyte-stimulating activity. As reported by Noble and Murray (1984) for neonatal rat optic nerve oligodendrocytes, type 1 astrocyte conditioned media from cells after six passages in vitro increased the number of oligodendrocytes, but to a lesser extent than equivalent volumes of B104 conditioned medium.

Figure 5:
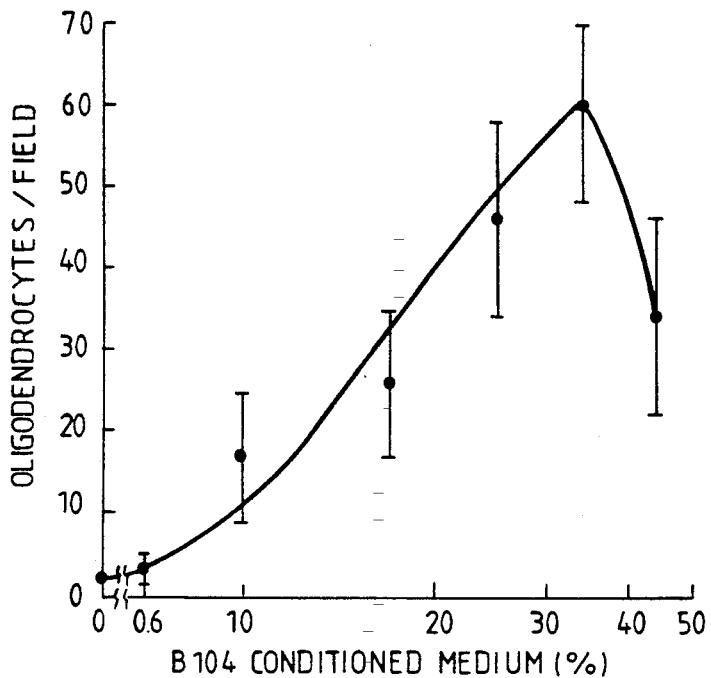
FIG. 5: Dose-dependent effect of various percentages of B104 conditioned medium added to O1 medium on the number of dissociated neonatal rat brain oligodendrocytes per field ($\times 200$) after 7 days in vitro. Oligodendrocytes are defined as 8–12 micron cell diameter, process-bearing cells. Data are shown as the mean $\pm SD$ of 5 fields.

A dose-dependent relationship between the percentage of B104 conditioned medium and the number of morphologically identified oligodendrocytes after 7 days in vitro is shown in FIG. 5. A maximum 30-fold increase is seen with 33% conditioned medium (about 8 μg protein/ml). Higher percentages result in fewer oligodendrocytes, suggesting an active inhibitory effect or dilution of 01 components. Subsequent experiments in which 01 or 03 supplements were kept constant at 100% levels with various concentrations of conditioned medium indicate the latter does not account for the diminished response. Moreover, equivalent amounts of protein from concentrated and dialyzed conditioned medium (Amicon DC2 hollow fiber unit with 5,000 $M_r$ cutoff) which do not significantly displace the volume of 03 medium have activity similar to the native conditioned medium. Using the same procedure used for showing an effect of adsorbed fibronectin by incubating dishes with 10 μg protein/ml (Bottenstein and Sato, 1980), the present inventors incubated polylysine-coated culture surfaces with 8 μg protein/ml B104 conditioned medium for 30 min., followed by extensive washing. This treatment has no effect on the number of oligodendrocytes maintained for 7 days in 03 medium, suggesting that in this protocol the active factors are soluble and non-absorbable or are inactive when adsorbed. Other data also suggest it is soluble factors that are active: removal of conditioned medium after cells are attached results in the generation of fewer oligodendrocytes.

Figure 6:
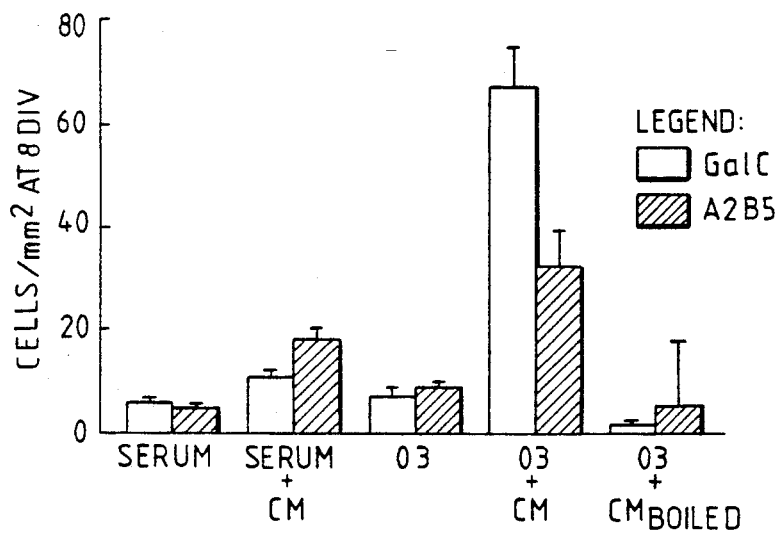
FIG. 6: Increased density of cells expressing GalC (a marker for oligodendrocytes) and A2B5 (a marker for glial progenitor cells) in response to 33% B104 conditioned medium (CM) in 15% calf serum-supplemented and serum-free O3 medium; heat sensitivity of the CM factors. In the control treatment 33% unconditioned medium (N4) is added to O3 medium. Heat treatment of CM was at 100 degrees C. for 20 min. Cultures were fixed at 8 days in vitro and immunostained for GalC and A2B5. Data are shown as the mean of fields counted $\pm SEM$. Ten to fifteen fields ($\times 200$; $0.3$ mm$^2$/field) were counted for each treatment.

FIG. 6 shows that B104 conditioned medium exerts an effect on cells expressing A2B5 (0-2A progenitor cell or early oligodendrocyte marker in neuron-free cultures; Bottenstein, 1986a; Raff et al., 1983) and GalC (oligodendrocyte marker) antigens even in the presence of 15% calf serum. There is a three-fold increase in A2B5-positive cells and a two-fold increase in GalC-positive cells after 8 days in vitro. Sister cultures containing 03 medium with 33% N4 medium (unconditioned B104 medium) have more A2B5-positive cells but similar numbers of GalC-positive cells compared to serum-supplemented cultures. Cells in 03 medium and 33% B104 conditioned medium are nine times more GalC-positive and four-fold more A2B5-positive than controls. Rat embryonic brain extracts (rich in neurons) also increase A2B5 and GalC expression in a dose dependent manner at 36–108 µg/ml.

The morphology and expression of GalC in neonatal rat brain cultures in 03 medium and 33% B104 conditioned medium is illustrated in FIG. 1. A representative field of robust, process-bearing cells is shown after 9 days in vitro; a sister field shows GalC-positive process-bearing cells, several of which exhibit membranous expansions. Cultures can be maintained in this condition for months with no loss of galactocerebroside expression and no overgrowth with Type 1 astrocytes.

Figure 7:
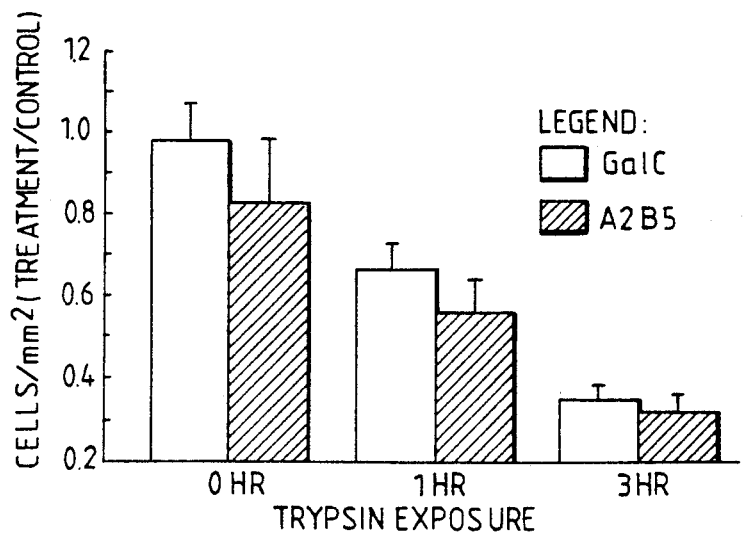
FIG. 7: Trypsin sensitivity of B104 conditioned medium (CM) factors as measured by the density of cells expressing GalC and A2B5. Conditioned medium was incubated with 0.3 $\mu g$ trypsin/ml CM for 0, 1, and 3 hr at 377° C. Then 0.6 $\mu g/ml$ soybean trypsin inhibitor (STI) was added and CM was incubated 1 hr more at 37° C. The control CM was incubated without trypsin first and then received STI as above. After treatment, the CM was stored at $-70°$ C. until use. Neonatal rat brain cells were cultured in O3 medium with 33% of the treated CM. Data are expressed as the ratio $\pm SEM$ of the density of antigen-positive cells in the trypsin-treated condition to the control condition. Control treatment densities were 10.2 GalC+ cells/mm$^2$ and 21 A2B5+ cells/mm$^2$.

Heat and Trypsin Sensitivity of B104 Conditioned Medium. Treatment of the conditioned medium at 100° C. for 20 min. significantly decreases (Wilcoxon rank sum test: $P < 0.05$) its activity (FIG. 7). FIG. 7 presents the effect of trypsin treatment of conditioned medium for 1 and 3 hr. Decreasing densities of GalC- and A2B5-positive cells (treatment/control) occur with increasing trypsin exposure; density of cells expressing these antigens is decreased about 70% after 3-hr treatment. These results demonstrate that the activity in B104 conditioned medium is dependent on protein moieties.

Effect of Other Medium Components. Compared to 0l medium alone, in the presence of 33% unconditioned medium (N2) there are similar numbers of morphologically identified oligodendrocytes. If 33% B104 conditioned medium is present, there is a marked increase in the number of these cells after 13 days in vitro (FIG. 8), suggesting that components of N2 medium do not increase the density of these cells. Indeed, the addition of equivalent amounts of the N2 supplements progesterone or putrescine to 0l medium have no effect on these cells. The transferring requirement could not be replaced by 1 µg/ml FeSO$_4$ as for B104 cells. The inventor also tested the effect of several factors shown by others to be growth-promoting for oligodendrocytes and other cell types. Addition of 5 ng/ml fibroblast growth factor or 0l medium results in fewer oligodendrocytes at 7 day in vitro and their disappearance by 22 days in vitro. One millimolar pyruvate in 0l medium elicits more type 1 astrocytes and no oligodendrocytes are present after 16 days in vitro. If $10^{-8}$ M triiodothyronine (T$_3$) is added to 0l medium or medium containing 15% calf serum, a five-fold reduction in oligodendrocytes occurs after 15 days in vitro. The influence of pyruvate or T$_3$ is shown in FIG. 8 after 13 days in vitro. Moreover, little or no effect on the number of oligodendrocytes is observed if the following components are added to 0l medium: 12.5 µg/ml fatty acid-free bovine serum albumin (FAF-BSA); 0.1 µg/ml lipoic acid, docosahexaenoic acid, linoleic acid, linolenic acid, or arachidonic acid with 12.5 µg/ml FAF-BSA; 5 µM ethanolamine; 10–100 µg/ml choline chloride, 100–1,000 µg/ml myo-inositol, or various combinations of choline and myo-inositol; or 0.1–100 ng/ml astrocyte growth factor 2 (Pettman et al., 1982) in the presence or absence of B104 conditioned medium.

Figure 9:
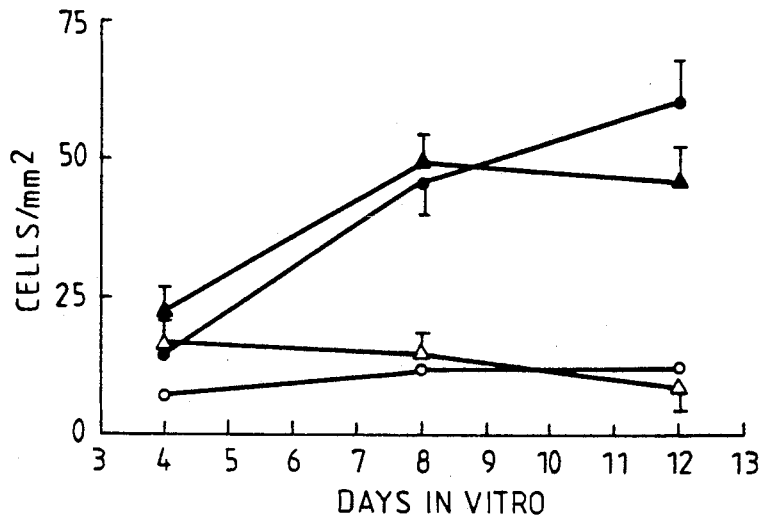
FIG. 9: Changes in cell density over time in response to O3 medium with 33% B104 conditioned medium (CM) or 33% unconditioned medium (N4). open circle, GalC+ cells/N4; closed circle, GalC cells/CM; open triangle, A2B5+ cells/N4; closed triangle, A2B5+ cells/CM. Data are expressed as the mean of fields.
Figure 10:
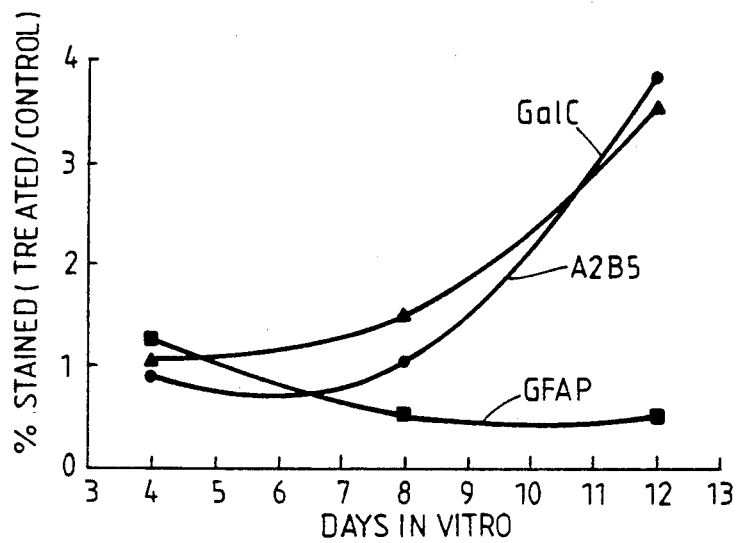
FIG. 10: Ratios of immunostained cells in treated (O3 medium with 33% B104 conditioned medium) vs. control (O3 medium with 33% unconditioned N4 medium) cultures over time. Percentages of cells immunostained for GalC, A2B5, or GFA (a marker for type 1 and type 2 astrocytes) were evaluated by counting total cells with phase contrast optics and immunostained cells in the same field with fluorescence optics.

Time course of the effect of B104 conditioned medium. FIG. 9 represents the expression of A2B5 and GalC in neonatal cultures on days 4, 8, and 12 in the absence and presence of B104 conditioned medium. In unconditioned medium there are more A2B5-positive than GalC-positive cells on day 4, but thereafter A2B5 expression drops about two-fold between days 4 and 12, whereas GalC expression is increased by an equivalent amount. This is consistent with a conversion of some A2B5 progenitor cells into the more differentiated oligodendrocyte phenotype or of a decrease in A2B5-positive cell survival and stimulation of GalC-positive cell division. In contrast, in the B104 conditioned medium-treated cultures the density of A2B5-positive cells increases about two-fold from day 4 to 8 and remains at that density between days 8 and 12, while the density of GalC-positive cells increases about four-fold between days 4 and 8 and continues to increase to about five-fold by day 12. If the data is expressed a different way as the number of immunostained cells/total cells enumerated with phase contrast microscopy (33% B104 conditioned medium/33% unconditioned medium), a clear rise in the expression of both A2B5 and GalC is evident over the 12-day treatment period (FIG. 10).

When glial fibrillary acidic protein (GFA)-positive cells were counted during this same time interval (FIG. 10), there was a significant drop in the percentage of these immunostained cells. Since only a small percentage of the cells in either treatment were both A2B5-positive and GFA-positive, characteristic of type 2 astrocytes, this suggests a decrease occurs in the percentage of type 1 astrocytes that are A2B5-negative and GFAP-positive. Type 2 astrocytes are not observed at 4 days in vitro, and at 8 or 12 days in vitro in 03 medium with 33% B104 conditioned medium, double immunostaining for A2B5 and GFA shows the vast majority of A2B5-positive cells are GFA-negative. At 12 days in vitro, 4% of the multipolar, process-bearing A2B5-positive cells exhibit sufficient GFA-specific fluorescence to classify them as Type 2 astrocytes. A further 10% of A2B5-positive cells show very faint and diffuse cytoplasmic, nonfibrillar GFA immunostaining, and the inventor does not classify these cells as type 2 astrocytes.

Combined autoradiography and double immunostaining. This technique was used to assess the number of A2B5-positive and/or GalC-positive cells labelled with tritiated thymidine between days 10 and 12. Table II shows 20% of the cells do not express either antigen, 19% are A2B5-positive but GalC negative, 53% are both A2B5-and GalC-positive, and only 7% are A2B5-negative but GalC-positive. These antigen profiles correlate with type 1 astrocyte/other, progenitor cell/type 2 astrocyte, early oligodendrocyte, and more mature oligodendrocyte, respectively. Only 8% of the negative cells are labelled, whereas 50% of the putative progenitor cells are labelled, 58% of the early oligodendrocytes are labelled, and 70% of the more mature oligodendrocytes have labelled nuclei. However, the 48-hr pulse length provides sufficient time for progenitor cells and early oligodendrocytes to further differentiate into more mature phenotypes. If the pulse time is shortened to 24 hr. the labelling index for the cells expressing A2B5 or GalC is shifted toward the less differentiated phenotypes, suggesting mature oligodendrocytes are not targets for the growth-stimulating effect of B104 conditioned medium. Additional experiments set forth below confirm this finding.

TABLE II

Thymidine Incorporation by Neonatal Rat Brain Cells of Different Antigenic Profile at 12 Days in Vitro

| Silver grains | A2B5/GalC− | A2B5+/GalC | A2B5+/GalC+ | A2B5−/GalC+ | Total (%) |
|---|---|---|---|---|---|
| − | 18.9 | 9.4 | 22.6 | 2.2 | 53.2[a] |
| + | 1.6 | 9.4 | 30.7 | 5.1 | 46.8[b] |
| Total (%) | 20.5[c] | 18.8[d] | 53.3[3] | 7.3[f] | 100.0 |

A total of 371 cells were counted in three different fields. Silver grain-positive cells had ≧10 grains/nucleus. Cell inocula: 395,000 cells/0.79 cm² in O1 medium with 33% B104 conditioned medium. Cultures were pulsed with 1 μCi/ml ³H-thymidine for 48 hr before fixation, double immunostaining for A2B5 and GalC antigens, and processing for autoradiography. Slides were developed after 5 days at 4° C. Data were analyzed by computer-aided image analysis of superimposed phase contrast, A2B5+-fluorescein, and GalC+-rhodamine images from three separate negatives of an identical field.
[a]% of cells without silver grains.
[b]% of cells with silver grains.
[c]% of A2B5/GalC cells.
[d]% of A2B5+/GalC− cells.
[e]% of A2B5+/GalC+ cell.
[f]% of A2B5/GalC− cells.

Figure 11:
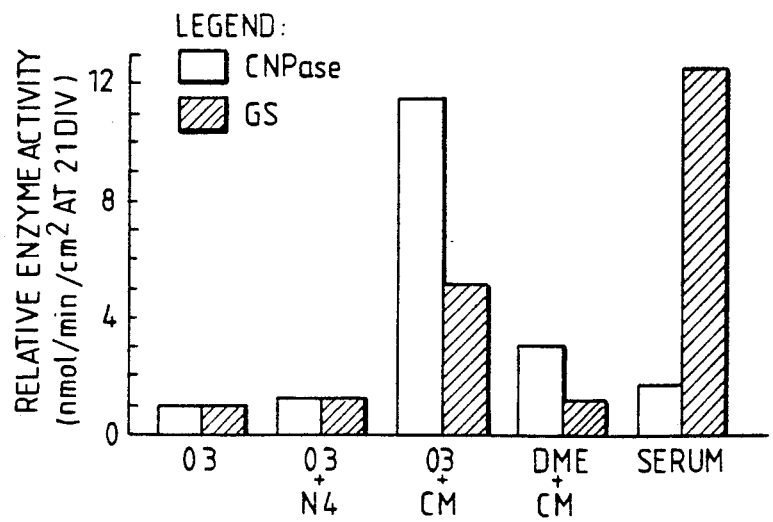
FIG. 11: Relative activities of the oligodendrocyte marker 3',5'-cyclic nucleotide 3'-phosphodiesterase (CNPase) and the astrocyte marker glutamine synthetase (GS) in dissociated neonatal rat brain cultures plated in different media. Cultures contained the indicated differences in culture medium. Medium was changed every 4 days and cultures were harvested after 21 days in vitro. 33% unconditioned medium (N4) or 33% B104 conditioned medium (CM) was added to O3 medium or the basal medium (DME). Serum containing cultures consisted of 15% calf serum added to DME. Data are expressed as the mean nmol product/min/cm$^2$ of triplicate samples from pooled harvests of three 25-cm$^2$ flasks.
Figure 13A:
FIG. 13A–D: Fluorescence micrographs of 12 DIV neonatal rat brain cultures. Cells were maintained in 33% B104 conditioned medium/67% O3 medium and immunostained. (A,C) A2B5; (B) galactocerebroside (GalC); (D) glial fibrillary acidic protein (GFAP). Comparing identical fields in (A) and (B), several multipolar A2B5-positive cells are present that are not GalC-positive (arrows) and GalC-positive cells show no or weak A2B5-positivity; or in (C) and (D), most A2B5-positive cells show no or slight, non-fibrillar GFAP-reactivity in the perinuclear region, the type 1 astrocytes (A2B5-negative, GFAP-positive) exhibit a fibrillary pattern of GFAP in the cytoplasm, and several type 2 astrocytes (A2B5-positive, GFAP-positive, arrows) are evident. Bar, 20 μm.
Figure 13B:
Figure 13C:
Figure 13D:
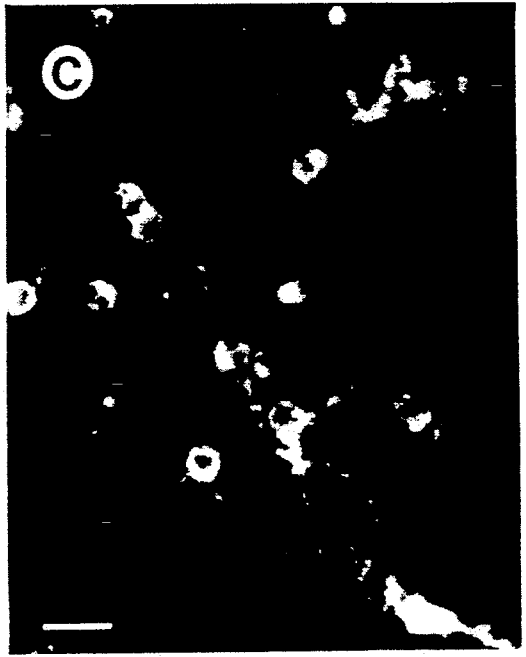

Glial enzymatic activity. FIG. 11 indicates the oligodendrocyte-specific 2′,3′-cyclic nucleotide 3′-phosphodiesterase (CNPase) activity in O3 medium is unaffected by addition of unconditioned medium, but after 21 days in vitro it increases 12-fold in response to B104 conditioned medium. Even when the O3 supplements are missing, B104 conditioned medium still increases CNPase activity about three-fold, and in the presence of 15% calf serum the enzyme activity is increased twofold. These data suggest both O3 supplements and conditioned medium are important for optimal expression of CNPase activity in these cultures. Addition of $10^{-8}$ M zinc sulfate further increases CNPase activity two-fold, while $10^{-8}$ M $T_3$ and $10^{-10}-10^{-08}$ ea copper sulfate have no effect. The astrocyte-specific glutamine synthetase (GS; Norenberg and Martinez-Hernandez, 1979) activity also does not appear to be influenced by unconditioned medium. However, GS activity is elevated about 5-fold in the presence of O3 supplements and conditioned medium, is unaffected when treated with conditioned medium alone, and is increased about 13-fold in the serum supplemented condition. These data indicate optimal GS activity occurs in the presence of 15% calf serum as expected, since more type 1 astrocytes are observed in this condition. On the other hand, type 1 astrocytes are more differentiated in the presence of the conditioned medium; they express more GFA at earlier times and they show extensive formation of long GFA-positive processes not seen in the control cultures.

Additional morphological and antigenic characterization of cultures. At 4 days in vitro (DIV), cultures treated with 33% B104 conditioned medium (CM) contain abundant numbers of small, A2B5-positive, bipolar glial progenitor cells, which appear to be highly mitotic. Control cultures treated with 33% unconditioned (N4) medium show few bipolar A2B5-positive cells at this time. FIG. 12 demonstrates the appearance of A2B5-positive cells in the presence of 33% CM. A shift in the morphology of the A2B5-positive population takes place by 8 DIV, and the predominant phenotype is multipolar, suggesting that these cells arise from the bipolar ones. As reported above, double immunostaining studies of CM-treated cultures indicate that most A2B5-positive cells are negative for GalC and GFAP, indicating that large numbers of glial progenitors are present. A small number of GalC-positive oligodendrocytes are present at 4 DIV in CM-treated cultures and are a mixture of bipolar and multipolar phenotypes. In contrast, oligodendrocytes in the control cultures at 4 DIV are more morphologically differentiated with predominantly multipolar, highly branched processes.

Quantitative analysis of cell types at 4 and 8 DIV (Table I) indicates that the 0-2A lineage cells (glial progenitors and their progeny: oligodendrocytes and type 2 astrocytes) increase in number in response to CM, but type 1 astrocytes, microglia, and other cell types (Thy1.1-positive) do not. The greatest differences between control and CM-treated conditions are in the progenitor population--12 to 15-fold increases. The increase in the progenitor population accounts for 85% of the increase in 0-2A lineage cells at 4 DIV and 44% at 8 DIV, whereas oligodendrocytes account for 11% of the increase at 4 DIV and 49% of the increase at 8 DIV. Cells expressing both A2B5 and GFAP (type 2 astrocytes) are increased at 8 DIV due to CM-treatment, but the proportion they represent in total 0-2A lineage cells is not different (Table III), indicating that differentiation of progenitors into type 2 astrocytes by the CM is not enhanced. In contrast, oligodendrocytes are a smaller fraction of the total 0-2A lineage in CM-treated cultures, suggesting that differentiation into this phenotype is retarded.

TABLE III

Percentages of cells in the oligodendrocyte/type 2 astrocyte lineage.

| | % of total O-2A lineage cells ± SEM (% of total cells) | | | |
|---|---|---|---|---|
| | 4 DIV | | 8 DIV | |
| Cell Type | Control | Treated | Control | Treated |
| Progenitors | 11 ± 4 | 58 ± 5[c] | 14 ± 5 | 37 ± 4[b,e] |
| Type 2 Astrocytes | 13 ± 2 | 7 ± 2 | 10 ± 3 | 7 ± 1 |
| Early Oligodendrocytes | 55 ± 6 | 31 ± 5[b] | 25 ± 5[e] | 36 ± 4 |
| Late Oligodendrocytes | 21 ± 1 | 5 ± 1[a] | 51 ± 8[f] | 19 ± 3[c,f] |
| Total Oligodendrocytes | 76 ± 6 | 34 ± 3[c] | 76 ± 5 | 55 ± 5[c,e] |

Culture preparation, cell identification, and statistical analysis are as described in Table I.

Although the numbers of oligodendrocytes and type 2 astrocytes do not differ significantly between control and CM-treated conditions at 4 DIV, they do at 8 DIV, suggesting that differentiation of the progenitor population takes place principally at 4-8 DIV. Cultures treated with concentrated/dialyzed CM for 12 days show little difference in cellular phenotypes from those cultures treated with crude CM for 8 days. In 12 DIV cultures, 93% of the GalC-positive cells are double-immunostained for myelin basic protein, a marker for mature oligodendrocytes. FIG. 13 shows double immunostains for A2B5/GalC and A2B5/GFAP in 33% CM-treated cultures at 12 DIV. Multipolar A2B5-positive cells which are not GalC-positive or GFAP-positive are present. Type 1 astrocytes in CM-treated cultures exhibit longer processes and brighter GFAP staining than control-treated cultures at equivalent times in vitro (data not shown), although there are no differences in their numbers between treatments.

When cellular debris and erythrocytes are removed from the cell suspension by centrifugation on a Percoll gradient before plating, resulting cultures also contain numerous A2B5-positive cells at 3 DIV (FIG. 12A). This indicates that factors derived from cellular debris probably play no role in the CM factor action. Moreover, if these gradient-processed cells are plated at higher density, most A2B5-positive cells are multipolar (FIG. 12C) instead of bipolar at 3 DIV, suggesting that density affects process morphology.

Figure 14A:
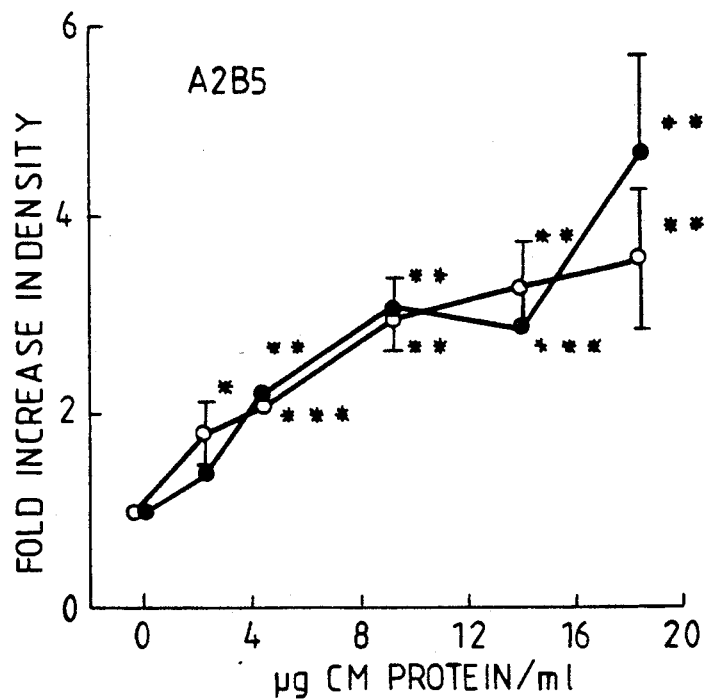
FIG. 14: Responses of A2B5-positive and galactocerebroside (GalC)-positive populations at 4 and 8 DIV to B104 conditioned medium (CM). Cells were cultured and immunostained. Twenty-six fields (400×) were counted for A2B5 and thirteen fields (200×) for GalC. The fold-increase in cell density ±SEM over the corresponding control culture (containing an equivalent volume of unconditioned N4 medium) is plotted against the concentration of conditioned medium protein.(○) 4 DIV; (●) 8 DIV. Each data point is the mean from 3-4 cultures. Significant changes from control according to Student's t test are: *$p<0.05$, $p<0.01$, *$p<0.001$.
Figure 14B:
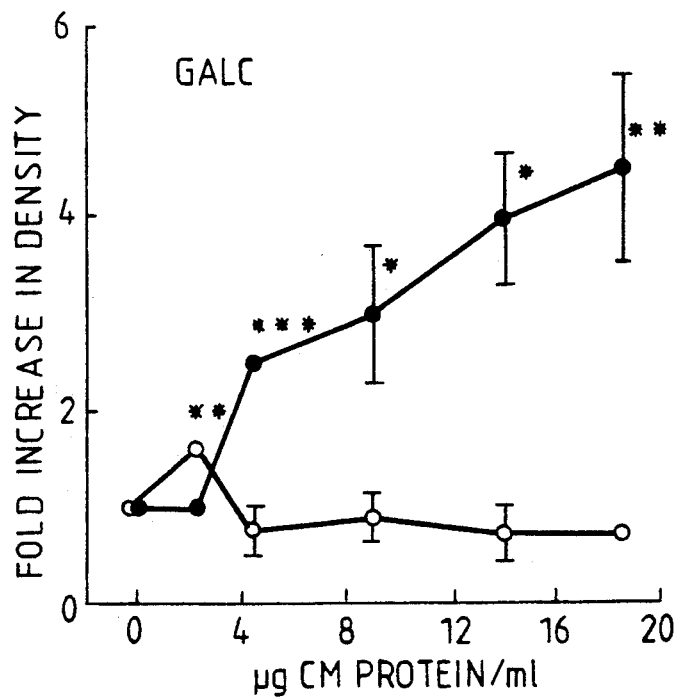

Changes in CM factor concentration affect number of progenitors and oligodendrocytes. The effect of different CM concentrations on the density of A2B5-positive (virtually all progenitors and early oligodendrocytes) and GalC-positive (oligodendrocytes only) cells at 4 and 8 DIV was investigated. A strong dose-dependence for both populations is evident at 8 DIV (FIG. 14), and no preferential effect on either population could be detected. In contrast, a marked preferential action of CM factors on the A2B5-positive population was seen at 4 DIV. At this time the increase in A2B5-positive cell density was similar to that at 8 DIV, but the GalC-positive population did not respond (except at 2 µg/ml). The responsive cells at 4 DIV are virtually all GalC-negative, GFAP-negative, bipolar glial progenitors, and their density is positively correlated with the quantity of CM present. The initial selective expansion of the A2B5-positive population suggests that later increases in oligodendrocytes are dependent upon this earlier event.

Since low molecular weight substances could potentially modify the response, the inventor tested concentrated/dialyzed CM ($M_r$ cutoff 5 kilodaltons [kd]). This preparation, at 4–16 µg protein/ml (Table IV), produced a response in the A2B5-positive population at 4 DIV similar to that produced by 8–66% crude CM (3–18 µg protein/ml). In addition, GalC-positive cell densities at 4 DIV correlate negatively with the does of concentrated/dialyzed CM. No change in GalC-positive densities in spite of elevated numbers of A2B5-positive cells suggests a delay in differentiation of progenitors due to CM treatment. These experiments confirm that both crude and concentrated CM have a dose-dependent effect on the A2B5-positive population, and that neither substances in the CM of less than 5 kd nor putrescine and progesterone (contained in N4 medium) are required for the response.

TABLE IV

Increases of A2B5-positive and galactocerebroside (GalC)-positive cells at 4 DIV in response to concentrated/dialyzed B104 conditioned medium (CM).

| µg CM protein/ml | Fold increase ± SEM (N = 5) | |
|---|---|---|
| | A2B5-positive | GalC-positive |
| 0 | 1.0 ± 0.1 | 1.0 ± 0.0 |
| 4 | 1.8 ± 0.1 | 1.0 ± 0.1 |
| 8 | 2.2 ± 0.2$^a$ | 0.7 ± 0.2 |
| 12 | 2.9 ± 0.3$^b$ | 0.8 ± 0.1 |
| 16 | 2.9 ± 0.2$^b$ | 0.6 ± 0.1 |

TABLE IV Legend:
Dissociated neonatal rat brain cells were cultured in serum-free 03 medium and concentrated/dialyzed CM (>5 kd). An equal volume of phosphate buffer was added to the control. At 4 DIV, cultures were fixed and immunostained. Ten 200× fields (0.3 mm$^2$/field) in a strip were counted for A2B5-positive or GalC-positive cells. Control A2B5- and GalC-positive densities were 38 and 31 cells/mm$^2$, respectively. A2B5-positive cell density correlates positively with the concentration of CM protein, and GalC-positive cell density correlates negatively (Spearman's Rank Correlation, $p < 0.05$). The method of Bonferroni shows significant differences between experimental groups and controls:
$^a p < 0.05$;
$^b p < 0.01$.

Bipotentiality of responsive cells. The bipotentiality of the responsive cells was determined by growing cultures until 4 DIV in 33% CM (12 µg/ml) and then changing the medium to either the same condition (33% CM/67% 03 medium), a serum-free condition without CM (100% 03 medium), or a serum-containing condition without CM (10% fetal bovine serum/90% 03 medium). At 7 DIV cultures were fixed and evaluated by double immunostaining (Table V). After removal of CM, immature cells differentiate into oligodendrocytes in serum-free 03 conditions (2-fold increase in percentage of 0-2A lineage) or type 2 astrocytes in serum-containing conditions (6-fold increase in percentage of 0-2A lineage). Therefore, the immature, A2B5-positive cells at 4 DIV appear to be bipotential 0-2A progenitor cells.

TABLE V

Bipotentiality of glial progenitor cells at 7 days in vitro.

| Cell type | Cells/mm$^2$ ± SEM (% of O-2A lineage cells) | | |
|---|---|---|---|
| | CM | O3 | SERUM |
| Progenitors | 184 ± 21$^{b,d}$ (55) | 59 ± 13$^d$ (24) | 82 ± 13 (30) |
| Type 2 Astrocytes | 23 ± 3$^e$ (8) | 11 ± 1$^e$ (4) | 129 ± 11 (47) |
| Early Oligodendrocytes | 70 ± 6$^c$ (21) | 93 ± 23$^d$ (38) | 25 ± 1 (9) |
| Late Oligodendrocytes | 57 ± 9 (17) | 82 ± 23 (33) | 39 ± 4 (14) |
| Total Oligodendrocytes | 126 ± 9$^{b,d}$ (37) | 173 ± 7$^e$ (71) | 64 ± 7 (23) |
| Total O-2A lineage cells | 337 ± 21$^{a,c}$ (100) | 247 ± 20 (100) | 275 ± 26 (100) |

Table V Legend:
Dissociated neonatal rat brain cells were cultured in 33% B104 conditioned medium (12 µg protein/ml)/67% 03 medium, and at 4 DIV the medium was changed to either the same medium (CM), 03 medium without CM (03), or 10% fetal bovine serum/90% 03 medium without CM (serum). Cultures were fixed at 7 DIV, and glial phenotypes were assessed by indirect immunocytochemistry. Removal of the conditioned medium results in fewer progenitor cells and more differentiated phenotypes. Oligodendrocytes are increased in 03 medium and type 2 astrocytes in the serum-containing medium. This is the expected result if progenitor cells are bipotential. Statistically significant differences in mean densities were determined using Fisher's Least Significant Difference test. Compared to the 03 medium:
$^a p < 0.05$,
$^b p < 0.01$;
compared to the serum-containing medium:
$^c p < 0.05$,
$^d p < 0.01$,
$^e p < 0.001$.

Complement lysis. In order to further study the ancestry of the oligodendrocytes which appear in response to the conditioned medium, 33% CM-treated cultures were treated with A2B5 antibody and complement at 3-4 DIV, before the appearance of most oligodendrocytes in these cultures, but at a time when many A2B5-positive progenitor cells are present. Four days after treatment with A2B5 antibody and complement, the numbers of oligodendrocytes (GalC-positive) and A2B5-positive cells were decreased an average of 69% and 76%, respectively, as compared to complement treatment without antibody (Table VI). This treatment destroys the oligodendrocyte-producing population, supporting the assertion that the CM factor requires at least a subset of the A2B5-positive population for production of oligodendrocytes. GalC antibody-mediated complement lysis showed only an 8% decrease in the numbers of GalC-positive cells four days later, suggesting that few GalC-positive cells arise from other GalC-positive cells. Thus, the increased numbers of GalC-positive cells at 8 DIV arise mainly from the A2B5-positive, GalC-negative cells present at 4 DIV, and not from A2B5-negative cells.

seen in control cultures were rare in CM-treated conditions, and $^3$H-thymidine-labeled GalC-positive cells were invariably weakly GalC-positive and of an immature, bipolar form.

In control conditions, little $^3$H-thymidine incorporation is detected in the A2B5- or GalC-positive populations, but since GFAP-positive cells (virtually all type 1 astrocytes) proliferate, this treatment is clearly not detrimental to cell division in general. Even though the A2B5-positive cells respond through 12 DIV in CM-treated cultures, the percentage of labeled GFAP-positive cells decreases markedly after 4 DIV in both control and CM-treated cultures. This suggests that CM factors have no stimulatory effects on type 1 astrocyte proliferation. Instead, it appears that the CM factors are promoting proliferation specifically in the A2B5-positive population, while the GalC-positive population may have a responsive subpopulation at 4 DIV. These results are compatible with the data on cell density,

TABLE VI

Effects of complement (C') lysis with A2B5 or galactocerebroside (GalC) antibody at 4 days in vitro (DIV) on A2B5-positive and GalC-positive cells.

Fold increase ± SEM (% change relative to no antibody)

| Antibody | 1 day post-treatment | | 4 days post-treatment | |
|---|---|---|---|---|
| | GalC-Positive | A2B5-Positive | GalC-Positive | A2B5-Positive |
| None | 1.8 ± 0.1 | 1.8 ± 0.3 | 2.6 ± 0.2 | 2.9 ± 0.4 |
| GalC | 0.4 ± 0.1$^b$ (−77) | 1.5 ± 0.2 (−17) | 2.4 ± 0.2 (−8) | 3.1 ± 0.2 (+7) |
| A2B5 | 0.5 ± 0.1$^b$ (−72) | 0.5 ± 0.1$^a$ (−72) | 0.8 ± 0.1$^b$ (−69) | 0.7 ± 0.3$^b$ (−76) |

Table VI Legend:
Dissociated neonatal rat brain cultures were grown in 33% B104 CM (8 μg CM protein/ml) 67% 03 medium. At 4 DIV they were treated with antibody and complement or complement only, and fold changes in immunostained cells were assessed at one (5 DIV) and four days (8 DIV) post-treatment relative to a paired control without complement, conditioned medium, or antibody. Mean cell densities ± SEM of the control cultures were 60 ± 19 (GalC, 5 DIV), 116 ± 29 (A2B5, 5 DIV), 56 ± 24 (GalC, 8 DIV), and 77 ± 16 (A2B5, 8 DIV). At 8 DIV the GalC antibody and complement-treated cultures had no decrease in GalC-positive oligodendrocytes, while the A2B5 antibody and complement-treated cultures had a great decrease in oligodendrocytes. Data are from 2-5 replicates in at least 2 separate experiments. Control cultures containing CM but no complement showed no significant differences in densities of GalC- or A2B5-positive cells compared to complement and CM but no antibody (Student's t test). Statistical significance was measured by the method of Bonferroni:
$^a$p < 0.05,
$^b$p < 0.01.

Figure 15A:
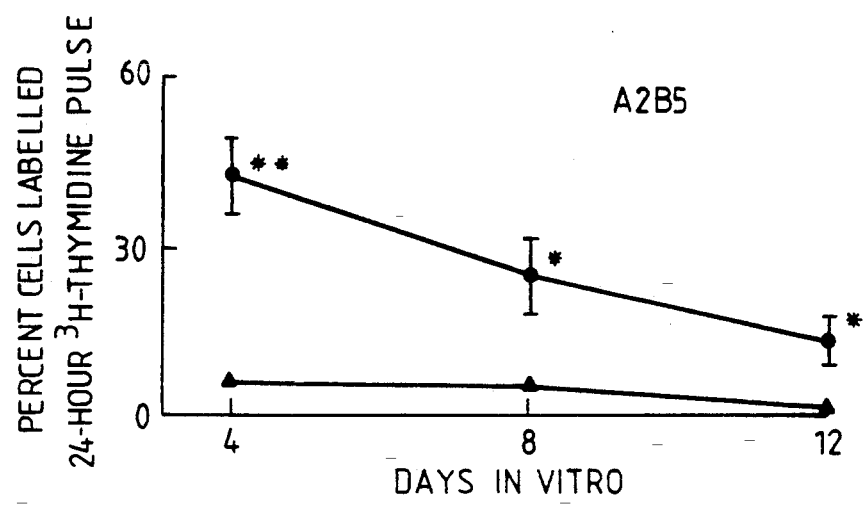
FIG. 15: Labeling indices of A2B5-, GalC-, and GFAP-positive populations in response to B104 conditioned medium (CM) or unconditioned (N4) medium treatment at 4, 8 and 12 DIV. Cultures in chamber slides were pulsed with $^3$H-thymidine (1 μCi/ml) for 24 h before fixation, immunostaining, and autoradiography as described. (Closed circle) 33% CM; (closed triangle) 33% N4. Replicate cultures (A2B5=4; GalC=3; GFAP=2) were evaluated at each point by examining 12-16 fields (400X). Values significantly different by Student's t test *$p<0.05$, **$p<0.01$.
Figure 15B:
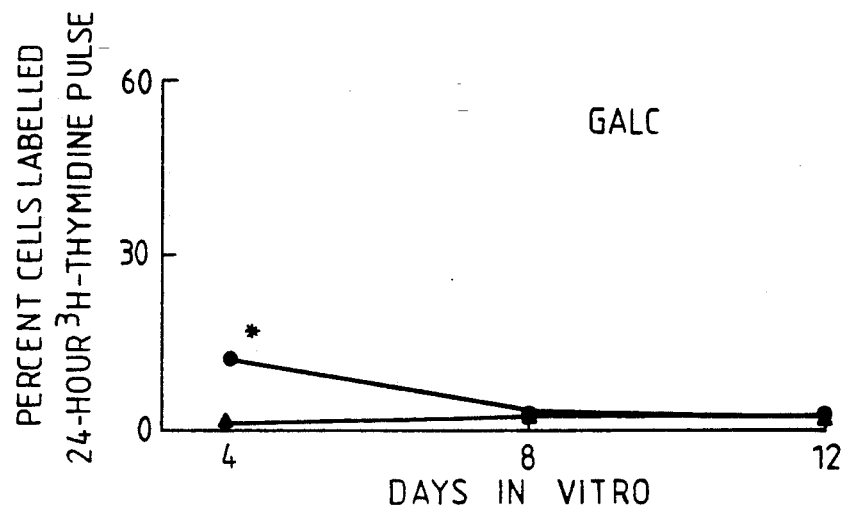
Figure 15C:
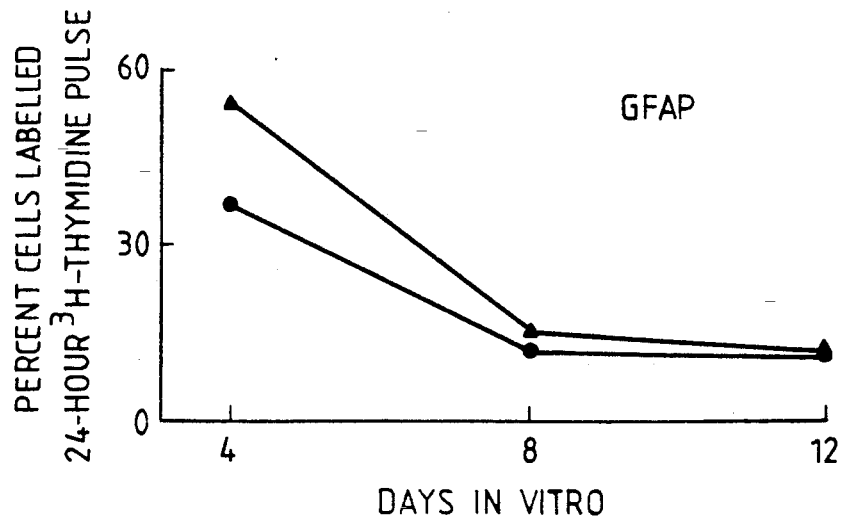
Figure 16A:
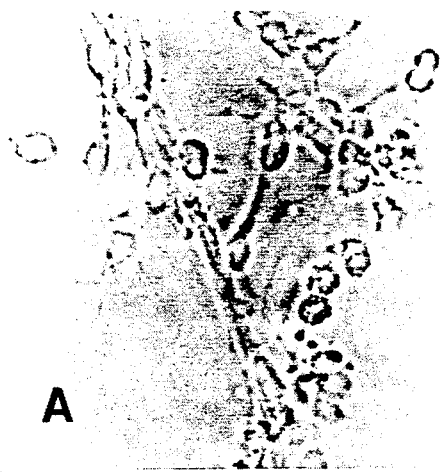
FIG. 16A–F: Phase-contrast and fluorescence micrographs of mechanically segregated astrocyte-enriched cultures (15 DIV). Cells were maintained in 33% B104 conditioned medium/67% N4 medium from 10-15 DIV. Culture procedures and double-immunostaining procedures are as described. The primarily astrocytic bed layer of serum-grown cultures was trypsin-detached and replated at 25 ×10$^3$ cells/cm$^2$ in 33% B104 CM/67% N4 medium. Two different fields are shown: (A,B,C) phase-contrast, A2B5 immunostain, and GFAP immunostain; (D,E,F) phase-contrast, A2B5 immunostain, and GalC immunostain. The phase-contrast micrographs (A,D) show small bipolar cells lying over and around type 1 astrocytes. Note in (C) that long bundles of GFAP-positive astroglial processes traverse the field, while only a few of the A2B5-positive cells exhibit any GFAP-reactivity. In (F), a few A2B5-positive cells show reactivity with anti-GalC. A companion culture without CM (100% N4) showed only rare A2B5-positive or GalC-positive cells. Bar, 20 μm.
Figure 16B:
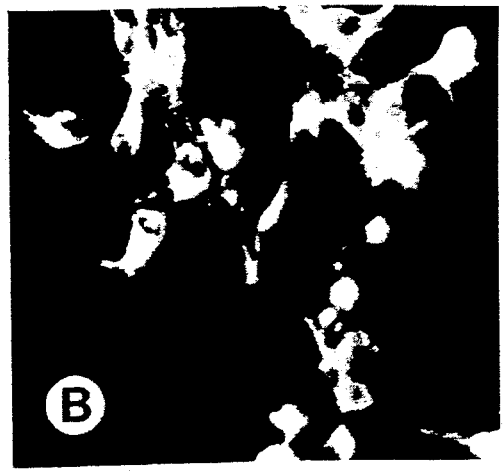
Figure 16C:
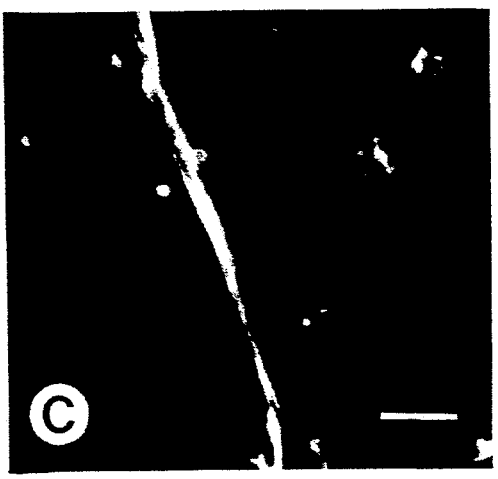
Figure 16D:
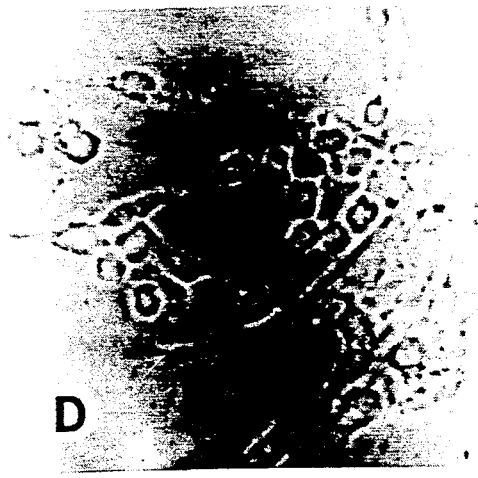
Figure 16E:
Figure 16F:
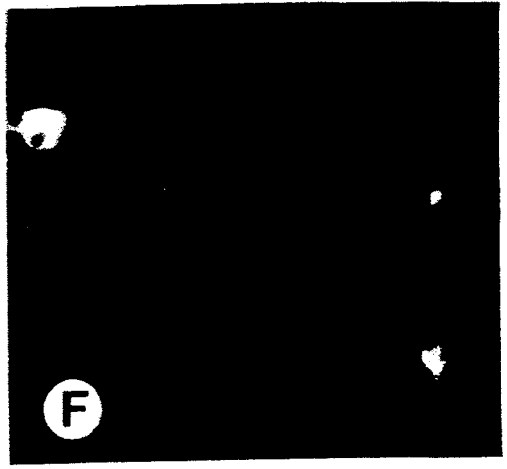

Thymidine incorporation by A2B5-positive, GalC-positive, and GFAP-positive populations. Experiments were performed to determine which cells respond to CM treatment by exposing cultures to a $^3$H-thymidine pulse prior to fixation. Studies set forth above indicated that 48-h $^3$H-thymidine pulses labeled both immature and mature phenotypes. An exposure of this length does not provide the resolution necessary to discriminate proliferating cells from labeled progeny. The pulse length was shortened to 24 h. Examples of labeling of the A2B5-positive cells are shown in FIG. 12E and 12G. The percent of A2B5-, CalC-, and GFAP-positive phenotypes incorporating $^3$h-thymidine in a 24-h pulse at 4, 8, and 12 DIV is depicted in FIG. 15. Significant increases are seen in labeling indices of the A2B5-positive population in CM treatments versus control unconditioned medium (N4)-treatments at 4, 8 and 12 DIV, but not in the GalC-positive populations (except at 4 DIV). In the presence of 33% CM, 45% of the A2B5-positive population are labeled at 4 DIV and 15% at 12 DIV. At 4 DIV, 13 % of the GalC-positive population labeled in CM, but only 2% in the control; at 8 and 12 DIV, no difference was detected between CM and control conditions in GALC-positive labeling indices. At 4 DIV, the strongly GalC-positive, multipolar, branched process-bearing oligodendrocytes usually indicating a preferential effect on the progenitor cells.

Percentage of thymidine-labeled cells depends on dose of CM factors. Having established that immature populations exhibit response in CM-treated conditions, the inventor investigated whether CM factors increase $^3$H-thymidine labeling in a dose-dependent manner. Since labeling indices are highest at 4 DIV, and cultures are not yet at maximal density, this time point was selected for analysis. Initially, different amounts of crude CM are compared with unconditioned medium (N4) controls (Table VII), and subsequently concentrated/dialyzed CM is used (Table VIII). Similar results are obtained with either preparation. The A2B5-positive population shows labeling indices of 43% in the presence of 10 μg crude CM protein/ml and 52% with 12 μg concentrated/dialyzed CM protein/ml. This series of experiments employs short, 6-h terminal $^3$H-thymidine pulses in order to further distinguish labeled GalC-positive cells from labeled progenitors that subsequently differentiate. An example of 6-h labeling of A2B5-positive cells can be found in FIG. 12B. Further classification of the 0-2A lineage cells by double immunostaining indicates that the progenitor population (A2B5-positive, GalC-negative, GFAP-negative) is the most responsive.

TABLE VII

Labeling indices at 4 DIV of neonatal glial cultures treated with unconcentrated conditioned medium (CM) versus unconditioned medium (N4).

| | % $^3$H-thymidine-labeled cells (labeled cells/total cells) | | | |
|---|---|---|---|---|
| | CM-treated | | N4-treated | |
| % CM or N4 | A2B5-positive | GalC-positive | A2B5-positive | GalC-positive |
| 16% | 15% (259/1685) | 5% (5/103) | 12% (101/882) | 5% (4/99) |
| 33% | 43% (1276/3001)$^a$ | 7% (5/74) | 12% (133/1142) | 7% (5/74) |
| 50% | 52% (1862/3594)$^b$ | 6% (5/79) | 10% (139/1462) | 5% (4/99) |

Table VII Legend:
Dissociated neonatal glia were cultured in chamber slides in serum-free O3 medium to which varying percentages of either B104 CM or N4 were added. The protein values represented by 16, 33, and 50% B104 CM are 5, 10, and 15 μg CM protein/ml, respectively. At 4 DIV cultures were exposed to 1 μCi/ml $^3$H-thymidine for 6 h before fixation. Cells were processed for immunostaining and autoradiography. Labeling indices were determined from 12–16 fields (400×) in 2 cultures. Significance was determined by Chi-square analysis:
$^a$p < 0.05,
$^b$p < 0.01.

TABLE VIII

Labeling indices at 4 DIV of neonatal rat brain cultures treated with concentrated/dialyzed B104 conditioned medium (CM).

| | % $^3$H-thymidine labeled cells ± SEM | | | |
|---|---|---|---|---|
| μg/ml | Total A2B5$^+$ | Total GalC$^+$ | A2B5$^+$ GalC$^+$ | A2B5$^+$ GalC$^-$ GFAP$^-$ |
| 0 | 10.7 ± 2.4 | 2.9 ± 1.2 | 4.2 ± 1.7 | 24.7 ± 5.0 |
| 4 | 37.6 ± 0.6$^a$ | 7.9 ± 1.5 | 15.2 ± 1.8$^a$ | 46.7 ± 1.8$^a$ |
| 8 | 44.8 ± 1.7$^a$ | 9.3 ± 1.3 | 12.2 ± 1.8 | 63.0 ± 3.5$^a$ |
| 12 | 52.8 ± 2.4$^a$ | 11.7 ± 0.7$^a$ | 16.3 ± 0.9$^a$ | 68.4 ± 3.0$^a$ |
| 16 | 51.5 ± 1.5$^a$ | 12.3 ± 3.0$^a$ | 20.5 ± 3.1$^a$ | 68.8 ± 1.3$^a$ |

Table VIII Legend:
Cultures and conditioned medium were prepared. An equivalent volume of phosphate buffer was added to the control. At 4 DIV cultures were exposed to 1 μCi/ml $^3$H-thymidine for 6 h before fixation. $^3$H-thymidine labelling indices for O-2A lineage cells were determined (3–4 cultures in two separate experiments). Data are shown for cells expressing A2B5 (Total A2B5$^+$; progenitors, early oligodendrocytes, and type 2 astrocytes), galactocerebroside (Total GalC$^+$; all oligodendrocytes), both (A2B5$^+$/GalC$^+$; early oligodendrocytes), and A2B5 but no GalC or GFAP (A2B5$^+$/GalC/GFAP$^-$; progenitors). Labeling indices for the type 2 astrocytes (A2B5$^+$/GFAP$^+$) were 2.6-fold greater with 16 μg CM protein/ml. Late oligodendrocytes (A2B5$^-$/GalC$^+$) were unlabelled in all conditions. Significant differences from the buffer control were analyzed by the method of Bonferroni: $^a$p < 0.01. Unmarked differences were not significant p ≤ 0.05).

Although modest increases in the GalC-positive labeling indices is observed, these are about 5-fold less than the A2B5-positive labeling indices. This relationship persists even if the early oligodendrocytes are compared to the progenitor cells. Moreover, 97% of the labeled GalC-positive cells are also A2B5-positive, indicating the virtual absence of proliferating, mature, A2B5-negative, GalC-positive oligodendrocytes in the preparation. Although relatively few A2B5-positive, GFAP-positive cells are present, labeling indices are similar to those for early oligodendrocytes, varying from 10% in the absence of CM to 27% at 16 μg CM protein/ml. The labeled cells are immature and bipolar in form, and do not resemble the typical multipolar, stellate type 2 astrocytes. Glial progenitors are by far the most responsive in terms of $^3$H-thymidine incorporation. This indicates that the low A2B5-positive labeling indices observed in the control conditions are not due merely to the presence of large numbers of less proliferative, early oligodendrocytes.

Response of glia isolated from cultures grown in serum-containing media. Since cultures prepared with serum-containing medium provide the possibility for segregating the majority of type 1 astrocytes (bed layer) from the superficial oligodendrocytes, glial progenitors, and type 2 astrocytes, response of glial progenitors can be evaluated with substantially reduced numbers of type 1 astrocytes present. At 12 DIV, serum-free, primary neonatal glial cultures typically have 68–74% (control-treated) and 45–55% (33% CM-treated) GFAP-positive cells. Mechanical segregation of cultures maintained in serum-containing medium for 10 days produced secondary cultures which contained only 24% GFAP-positive cells, but 61% A2B5-positive cells after 4 days in 33% CM (14 DIV), a twelve-fold decrease in the ratio of GFAP-positive, A2B5-positive cells. Since type 1 astrocytes have been reported to produce mitogens for progenitor cells (Noble and Murray, 1984), interference of these substances or a mediation of the CM action by them should be considered. If reductions in the percentage of astrocytes diminish the effects of CM on glial progenitors, then type 1 astrocytes could be implicated as either contributing mitogens directly or mediating the CM action through paracrine factors. Conversely, an undiminished proliferative response in a population rich in progenitors and poor in type 1 astrocytes would discount an astrocytic role in this response; however, it is unknown how many astrocytes might be required to exert such an effect. Nevertheless, the inventor has pursued the matter for two reasons: 1) mechanically enriched cultures of oligodendrocytes and progenitors do have many fewer type 1 astrocytes per progenitor cell than primary cultures in 33% CM and 2) the responses of these 10 DIV cells to the CM factors might provide evidence as to whether responsiveness is extended beyond the first few days in culture.

The oligodendrocyte and progenitor fraction derived from 10 DIV serum-containing cultures have been replated into varying concentrations of CM, and labeling indices after a 6-h $^3$H-thymidine pulse have been determined. A clear response to dose results (Table IX); A2B5-positive secondary cells (14 DIV) respond to CM after a 4-day treatment with equal vigor as 4 DIV unfractionated primary cells. Concentrated/dialyzed CM Cm$_r$ cutoff 5 kd) at 12 μg/ml gives a similar labeling index of 59±5% in the A2B5-positive population. Therefore, chronologically older progenitors are not necessarily less responsive, as suggested by the A2B5-positive labeling indices at 12 DIV in FIG. 15. Decreasing labeling indices with time in primary cultures may instead be due to density-dependent inhibition, since the cultures become quite dense. Alternatively, decreased labeling at later times could be due to differentiation of responsive cells into non-proliferative A2B5-positive cells. Secondary cultures, in contrast to primary cultures, are plated at lower densities and would not exhibit density-dependent inhibition.

TABLE IX

Labeling indices of A2B5-positive cells after 4 days in secondary culture.

| CM or N4 | % $^3$H-thymidine-labelled A2B5-positive cells ± SEM | |
|---|---|---|
| % | CM | N4 |
| 16% | 27 ± 4$^a$ | 6 ± 3 |
| 33% | 41 ± 7$^b$ | 7 ± 2 |
| 50% | 55 ± 4$^c$ | 10 ± 1 |

Mechanically separated superficial cells from 10 DIV cultures grown in 15% calf serum were replated in 03 medium with B104 conditioned (CM) or unconditioned medium (N4). After 4 days, cultures (N = 4) were treated for 6 h with 1 μCi/ml $^3$H-thymidine, then fixed and processed for autoradiography. CM protein concentrations for 16, 33, and 50% are 5, 10, and 15 μg/ml, respectively. Significant differences by Student's test:
$^a$p < 0.05,
$^b$p < 0.01,
$^c$p < 0.001.

Not only is the percentage of type 1 astrocytes decreased in secondary cultures, but there is also a twelve-fold decrease in the ratio of GFAP-positive:A2B5-positive cells. Since CM action is undiminished, astrocytes probably do not mediate the response of progenitors. However, the cultures are not completely type 1 astrocyte-free.

When the progenitor-poor, type 1 astrocyte-rich bed layer of serum-containing cultures was trypsinized after removal of the superficial cells and replated at low density (5–25×10$^3$ cells/cm$^2$) in N4 medium, the few progenitors remaining did not appear to proliferate. However, when these low-density secondary astrocyte cultures were grown in medium containing 33% CM, the small numbers of residual progenitors present expanded greatly. FIG. 16 shows a CM-treated secondary type 1 astrocyte-enriched culture 5 days after replating (15 DIV), with abundant progenitors and long GFAP-positive astrocytic processes but very few GFAP-positive, A2B5-positive cells (type 2 astrocytes). These progenitors were GalC- and GFAP-negative, and could be induced to become GFAP-positive type 2 astrocytes if placed into serum-containing media after removal of CM (data not shown).

Effect of B104 conditioned medium on embryonic neurons in vitro. The inventor has also analyzed the effect of the neural progenitor regulatory factor on neurons. For those experiments, whole brains of embryonic rats were mechanically dissociated and plated at 31,200 cells/2 cm$^2$ in 300 μl of N2 medium (1:1 mixture of Ham's F12 and Dulbecco's modified Eagle's medium with 5 μg/ml bovine insulin, 100 μg/ml human transferrin, 30 nM selenite, 20 nM progesterone, and 100 μM putrescine) with the additions set forth in Table X. B104 conditioned medium was concentrated and dialyzed (Mr cutoff 10,000) against PBS. Three days after plating, cells were were stained for neuron-specific enolase (1:200 dilution) using standard indirect immunofluorescence methods. The results of those experiments, Table X, indicated that culture with the B104 conditioned medium caused an increase in the number of neurons that could be identified by neuron specific enolase.

TABLE X

EFFECT OF B104 CONDITIONED MEDIUM ON EMBRYONIC NEURONS IN VITRO

| TREATMENT | cells/mm$^2$ MEAN ± SD | % Control |
|---|---|---|
| EMBRYONIC DAY 13: | | |
| Phosphate Buffer | 103 ± 2 | 100 ± 2 |
| B104 CM, 8 μg/ml | 213 ± 5 | 207 ± 5 |
| EMBRYONIC DAY 14: | | |
| Phosphate Buffer | 133 ± 4 | 100 ± 3 |
| B104 CM, 8 μg/ml | 297 ± 14 | 233 ± 11 |

Table X Legend:
Whole brains of embryonic rats were mechanically dissociated and plated at 31,200 cells/2 cm$^2$ in 300 μl of N2 medium (1:1 mixture of Ham's F12 and Dulbecco's modified Eagles' medium with 5 μg/ml bovine insulin, 100 μg/ml human transferrin, sferrin, 30 nM selenite, 20 nM progesterone, and 100 μM putrescine) with the above additions. B104 conditioned medium was concentrated and dialyzed (Mr cutoff 10,000) against PBS. Three days after plating, cells are fixed with 3.7% paraformaldehyde and after permeabilization are stained for neuron-specific enolase (1:200 dilution) using standard indirect immunofluorescence methods.

Improved assay for the neural progenitor regulatory factor. Although the activity of B104 conditioned medium (CM) factors can be tested by immunostaining neonatal rat brain cells for A2B5 antigen present on glial progenitor cells, the inventor has developed a more rapid, convenient, and also serum-free microassay for the activity using the C62B glial cell line and a colorimetric method (Mosmann, 1983; Hansen et al., 1989). Cultured cells are incubated in the presence of a substrate to yield a colored reaction product which is measured with a microplate reader (spectrophotometer). The blank consists of wells with no cells but all other reagents present. The entire process occurs in a microwell with no transfer of materials. The microplates are first coated with poly-D-lysine as above and a 2×concentrated culture medium and sufficient affinity-purified human fibronectin to give 1 μg/cm$^2$ is added at 50 μl/well. This concentrated serum-free medium comprises the following: Dulbecco's modified Eagle's medium (DME) with 60 nM selenite, 20 ng/ml biotin, 100 μg/ml human transferrin, and 20 nM hydrocortisone. Fractions of B104 CM are added at 25 μl/well or controls of the appropriate buffer or solvent. Finally, C62B cells are removed by trypsinization from flasks prior to confluence at a passage number 40 or below, an equimolar amount of soybean trypsin inhibitor is added, cells are centrifuged to obtain a cell pellet, which is resuspended in DME, and 3600–7200 cells/well are plated in 25 μl. The final volume is 100 μl. After 3–4 days incubation at 37° C. in humidified chamber, the bioassay is started by adding 25 μl/well of the substrate MTT [3-(4,5-dimethylthiazol-2yl)-2,5-diphenyl tetrazolium bromide; Sigma #M2128] in PBS. Cells and substrate are incubated at 37° C. for 2–4 hours, followed by addition of 100 μl/well of the extraction buffer to solubilize the crystalline formazan product formed, incubation at 37° C. for an additional 20 hours, and finally absorbances at 570 nm (with 630 nm reference wavelength to correct for interwell optical variations) are obtained with a microplate reader for 4–5 samples/treatment. The extraction buffer consists of 20% (w/v) sodium dodecyl sulfate in 50% N,N-dimethyl formamide and 50% deionized water, pH 4.7. The absorbance values are correlated linearly with the number of cells/well, forming the basis of a cell proliferation assay suitable for detecting neural progenitor regulatory factor activity.

EXAMPLE II

Purification of Neural Progenitor Regulatory Factor From Conditioned Medium of B104 Neuroblastoma Cells.

Although the experiments set forth above describe the characteristic activity of the neural progenitor regulatory factor, they did not enable its preparation in pure form. Even though the B104 cells were grown in a serum free medium developed by the inventor, the supernatant from the cell cultures was contaminated with a number of proteins and other substances produced by the cells themselves. The exact nature of those contaminants was not known but a substantially purified preparation of the factor was desired for use.

The present inventor has now developed methodology enabling preparation of the factor in substantially purified form for the first time. Using these methods, the inventor has been able to prepare preparations of the factor that are substantially purer than the crude preparations of culture supernatant described above. These methods are set forth below.

As a preferred first step, the B104 cells are cultured on microcarrier beads and the conditioned medium harvested, concentrated, and dialyzed, essentially as set forth above. The concentrated dialyzed medium may then be purified by any of several individual purification schemes or, more preferably by a combination of such procedures.

In one procedure, concentrated/dialyzed B104 conditioned medium containing about 11 mg of total protein was shaken overnight (20 hr) with 5.5 g heparin-Sepharose CL-6B in 5 mM phosphate buffer with 50 mM NaCl (PBS) pH 7.4 prepared as set forth above in Example I. The neural progenitor cell regulatory factor bound to the heparin-sepharose under these conditions. The mixture was then loaded into a 1.5×9 cm chromatography column and a 0.05-2M linear NaCl gradient in PBS was applied to the column at a flow rate of 7 ml/hour. Two ml fractions were collected from the column and assayed for neural progenitor cell regulatory activity by two types of assay (1) immunostaining with the A2B5 antibody and (2) the improved assay employing MTT. As shown in Table XI and FIG. 17, about 0.7-0.8M salt caused the factor to elute from the column in substantially purified form. Recovery was about 71%.

Figure 18:
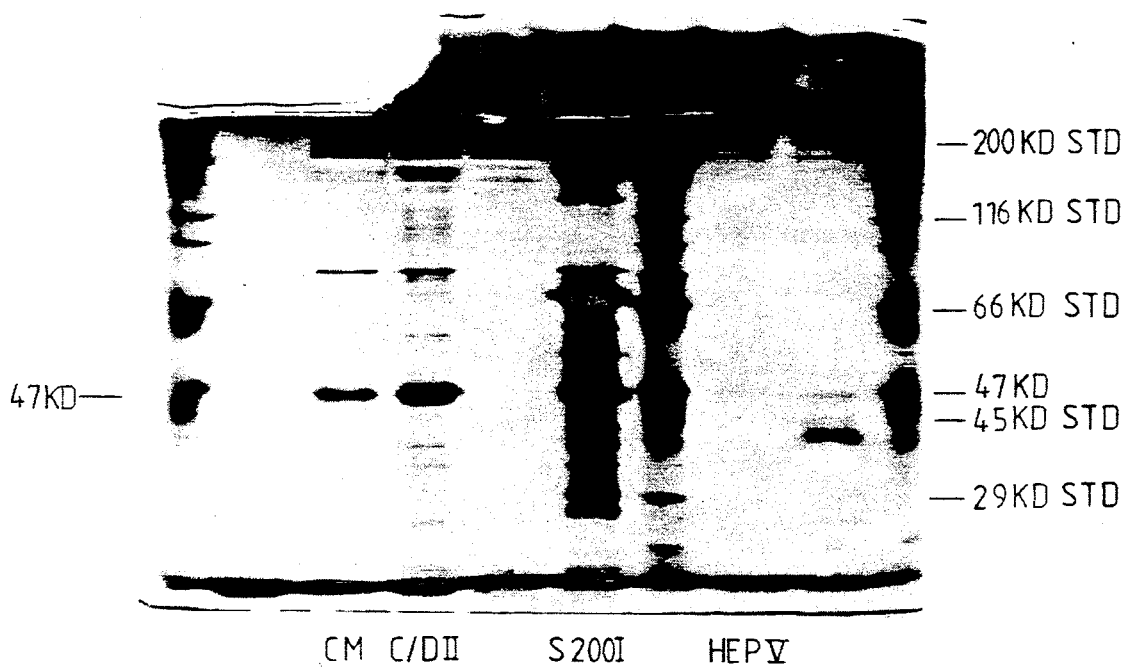
FIG. 18: 10% SDS-PAGE showing 47 KD neural progenitor regulatory factor. C/D is concentrated/dialyzed B104 conditioned medium (Mr cutoff 10,000); CM is B104 conditioned medium; S200I is gel filtration fractions 94-95; Hep V is heparin-Sepharose fraction 60-65 (eluted with 0.8–0.94 M NaCl).

Further, when factor-containing fractions from the column were analyzed by sodium dodecyl sulfate-polyacrylamide gel electrophoresis (SDS-PAGE) as shown in FIG. 18, a predominant band was observed at a position consistent with a molecular weight of 47 kilodaltons. The gel was stained with silver stain by known procedures.

In yet another procedure, conditioned dialyzed B104 conditioned medium containing about 1.9 mg of protein was loaded onto a 1.5×50 cm chromatography column containing Sephacryl S-200. The gel was run at a flow rate of about 15 ml per hour of PBS; and 0.5 ml fractions were collected and assayed with the 2 assays described above. Results are shown in Table XI and FIG. 17. The factor eluted from the column at a position consistent with a molecular weight of about 45 kilodaltons. Analysis of active fractions from this column by SDS-polyacrylamide gel electrophoresis showed a predominant band migrating at a position consistent with a molecular weight of about 47 kilodaltons (FIG. 18).

TABLE XI

| | | PROGENITOR REGULATORY FACTOR ATTRIBUTES | | | | |
|---|---|---|---|---|---|---|
| COLUMN | ASSAY | C/D S.A. UNITS/MG | PEAK S.A. UNITS/MG | FRACTION DESCRIPT. | INCREASE S.A. | PEAK CONC. |
| S-200 I | MTT | 4200 | 16040 | 46-47 Kd Mr | 4 | 132 ng/ml |
| | A2B5 | 238 | 8170 | 46-47 Kd Mr | 34 | 118 ng/ml |
| HEP VI | MTT | 2063 | 6076 | 0.7-0.8 M NaCl | 3 | 185 ng/ml |
| | A2B5 | 865 | 46640 | 0.7-0.8 M NaCl | 54 | 122 ng/ml |

Columns:
Sephacryl S-200 (superfine); 1.5 × 50 cm; flow rate 15 ml/hr; fractions 0.5 ml; load 1.9 mg C/D III; eluted with 5 mM phosphate buffer with 50 mM NaCl (PBS); recovery 86%.
Heparin-Sepharose CL-6B; 1.5 × 9 cm; flow rate 7 ml/hr; fractions 2 ml; 11 mg C/D V was shaken overnight with 5.5 g heparin-Sepharose in PBS; eluted with PBS and 0.05-2 M linear NaCl gradient; recovery 71%
Assay:
MTT is a colorimetric assay that measures cell number (Mosmann, 1983) and is performed with C62B glioma cells.
A2B5 is a cell surface antigen which identifies the glial progenitor cells that give rise to type 2 astrocytes and oligodendrocytes in the central nervous system. The number of A2B5-positive cells was determined using indirect immunofluorescence methods.
Abbreviations used include C/D (concentrated/dialyzed conditioned medium derived from B104 rat central nervous system neuroblastoma cells grown on microcarrier beads) and S.A. (specific activity expressed as units/mg protein; 1 unit equals a 100% increase over control after 4 days in culture).

In yet other experiments, concentrated/dialyzed B104 conditioned medium was electrophoresed through an SDS polyacrylamide gel using conditions set forth in FIG. 19. The 45-50 kd fraction was eluted from the gel overnight with shaking at 4 degrees in 150 microliters of PBS. This fraction was then tested for activity in the C62B-MTT assay. Using this assay, an 11% (p=0.03) increase in activity over control was observed. This less than optimal increase may be due to incomplete elution of the factor from the gel coupled with the presence of residual SDS and should be improved by a combination of electroelution and dialysis as described below.

As indicated, the procedures above may be combined to provide a potentially even more effective purification procedure. Thus in an additional embodiment, the active fractions eluted from the Heparin-Sepharose chromatography procedure are subsequently separated by gel exclusion chromatography, for example, over Sephacryl-200 as described to effect an even greater fold purification. Alternatively, the gel exclusion chromatography may be followed application of the active fractions to the heparin-Sepharose gel and selective elution therefrom.

As a third step in the purification of the neural progenitor regulatory factor, preparative SDS-PAGE coupled with electroelution can be used. The following prophetic example describes that procedure. Slab gels of the following dimensions can be used: 6 mm thick, 12 cm wide, 18 cm high. For this procedure samples are applied to a single slot and electrophoresed as in the minigel described in FIG. 20. Up to 10 mg of protein can be processed this way and 0.25-1.5 cm gel slices can be prepared after electrophoresis, followed by electroelution using a custom-made or commercial instrument (e.g. Fisher Biotech Gel Eluter) based on that first described by Posner 4976). In a few hours, 75-87% of the protein in a gel slice can be recovered vs. the approximately 10% recover obtained using passive diffusion (FIG. 20). If removal of SDS, which affects the bioassay and protein determinations, is not sufficient by dialysis against PBS, it can be achieved in two ways: (1) by electrophoretic dialysis as described by Tuszynski and Warren (1975) or (2) by anion exchange chromatography as described by Weber and Kuter (1971). The latter uses Dowex AG 1-X2 (200-400 mesh) from Biorad Laboratories. Prior to elution a narrow strip of the gel is silver stained using standard methods to locate protein standards and sample bands.

Alternatively, with the aid of the information provided by the present disclosure, a purification scheme utilizing reversed phase high pressure liquid chromatography (HPLC) could be employed. With that procedure, either a crude preparation of the factor, or preferably, a purified preparation derived from either a heparin affinity column, a gel exclusion column, or a combination of the two is applied to a suitable HPLC column, preferably a C3 column, equilibrated with a suitable hydrophilic solvent, for example, containing trifluoroacetic acid, and eluted with a gradient of increasing hydrophobicity, preferably, an acetonitrile gradient.

EXAMPLE III

Comparison of the Factor to Other Factors Reported to Stimulate Growth of Cells of the Central Nervous System The present inventor has also performed a number of additional experiments and analyses to further characterize the active factor and to differentiate it from other factors reported to stimulate proliferation of cells of the nervous system. These results, set forth in Table XII below indicate that the factor is partially destroyed by treatment with periodate, and by treatment with dithiothreitol followed by iodoacetamide but is resistant to treatment with urea. Activity of the factor is also not inhibited by treatment with antiserum specific for platelet derived growth factor, or acidic or basic fibroblast growth factors, indicating that it is distinct from those proteins.

TABLE XII

PROGENITOR REGULATORY FACTOR ACTIVITY AFTER VARIOUS CHEMICAL TREATMENTS

| TREATMENT | PERCENT CONTROL ($\pm$ SD) |
|---|---|
| Control Conditioned Medium (1 hr 37° C.) | 100 $\pm$ 21 |
| 5 mM Periodate (48 hr 1° C.) | 55 $\pm$ 8 |
| 0.25 mM Dithiothreitol (30 min 37° C.) followed by 0.5 mM Iodoacetamide (30 min 37° C.) | 41 $\pm$ 8 |
| 8 M Urea (30 min 37° C.) | 107 $\pm$ 8 |

Treatment of the conditioned medium was followed by a 17 hr dialysis against PBS. Cells from neonatal rat brains were dissociated mechanically and plated in serum-free 03 medium with B104 conditioned medium at 11 μg/ml. Cultures were stained for A2B5 antigen after 7 days in vitro using an indirect immunofluorescence method.
ANTIBODY TREATMENT
Polyclonal anti-Platelet Derived Growth Factor (PDGF; 33 μg/ml), anti-acidic Fibroblast Growth Factor (FGF;1:1000 dilution), and anti-basic FGF (1:1000 dilution) treatment did not diminish the activity of 2 μg/ml concentrated/dialyzed B104 conditioned medium, suggesting lack of identity with PDGF or FGF. Antibodies were preincubated with concentrated/dialyzed B104 conditioned medium (C/D III) for 30 min. at room temperature prior to addition to cultures of C62B cells in serum-free G1 medium. Effect on cell number was evaluated with the MTT colorimetric assay.

As shown in Table XIII, the factor may also be differentiated from Epidermal Growth Factor, Fibroblast Growth Factor, Glial Growth Factor, Glial Growth Promoting Factor, Glia Maturation Factor, Glia Promoting Factor 1, Glia Promoting Factor 3, Interleukin 1, Interleukin 2, Platelet Derived Growth Factor and Placental Derived Growth Factor based on molecular weight, target cells, and other characteristics.

TABLE XIII

| NAME | IDENTIFIED GLIAL GROWTH FACTORS | | PROPERTIES |
|---|---|---|---|
| | MOLECULAR WEIGHT | ISOELECTRIC POINT | |
| Epidermal Growth Factor | 6,000 | 4.6 | Heat-stable; targets: type 1 astrocytes |
| Fibroblast Growth Factor (acidic) | 17,000 | 6.0 | Heat-labile; binds heparin; homology with interleukin 1 beta; targets: type 1 astrocytes |
| Fibroblast Growth Factor (basic) | 15,000 | 8.5 | Heat-labile; binds heparin; homology with acidic FGF; targets: increases number of oligodendrocytes (may not be primary target) |
| Glial Growth Factor | 56,000 | 9.5 | Dimer, 31,000 subunit inactive; targets: type 1 astrocytes and Schwann cells but no effect on oligodendrocytes |
| Glial Growth Promoting Factor | 30,000 | — | After reduction the monomer is still active; targets: no effect on A2B5-positive cells, effect on galactocerebroside-positive oligodendrocytes |

TABLE XIII-continued
IDENTIFIED GLIAL GROWTH FACTORS

| NAME | MOLECULAR WEIGHT | ISOELECTRIC POINT | PROPERTIES |
|---|---|---|---|
| Glia Maturation Factor | 14,000 | 5.2 | Targets: type 1 astrocytes, some effect on O-2A progenitor cells |
| Glia Promoting Factor 1 | 15,000 | — | Targets: effect on both A2B5- and galactocerebroside-positive cells, no effect on type 1 astrocytes |
| Glia Promoting Factor 3 | 6,000 | — | Targets: effect on oligodendrocytes |
| Interleukin 1 | 18,000 | ? | Targets: type 1 astrocytes |
| Interleukin 2 | 25,000 | ? | Controversial: some report increased oligodendrocytes, others report decreased oligodendrocytes |
| Platelet Derived Growth Factor | 30,000 | 10.0 | Heat-stable; inactivated by reducing agents; 13,000 and 15,000 chains; targets: affects O-2A progenitor cells |
| Placental Derived Growth Factor | 60,000–80,000 | — | Heat-labile (85° C. 5 min): targets: type 1 astrocytes and A2B5-positive cells |

The foregoing description of the invention has been directed to particular preferred embodiments in accordance with the requirements of the patent statutes and for purposes of explanation and illustration. It will be apparent, however, to those skilled in the art that many modifications and changes may be made without departing from the scope and the spirit of the invention. It is the Applicants intention in the following claims to cover all such equivalent modifications and variations which fall within the true spirit, and scope of the invention.

REFERENCES

The following references may facilitate understanding of several aspects of the present invention. Inclusion of a reference in this list does not, however, constitute an admission that such reference represents prior art with respect to the present invention.

S. Federoff (1985): Macroglial cell lineages, In G. M. Edelman, W. E. Gall, W. M. Cowan, "Molecular Bases of Neural Development." New York; John Wiley, pp. 91–117.

B. P. Williams, E. Abney, M. C. Raff (1985). *Dev. Biol.* 112:126–134.

M. C. Raff, R. H. Miller, M. Noble (1983. *Nature* 303:390–396.

C. Ffrench-Constant, M. C. Raff (1986). *Nature* 319:499–520.

G. Levi, V. Gallo, M. Ciotti (1986). *Proc. Natl. Acad. Sci. USA* 83:1504–1508.

R. Pruss, P. Bartlett, J. Gavrilovic, R. Lisak, S. Rattray (1982). *Dev. Brain Res.* 2:19–35.

J. Brockes, G. Lemke, D. Balzer (1980). *J. Biol. Chem* 255:8374–8377.

M. Noble, K. Murray (1984). *EMBO J.* 3:2243–2247.

M. Noble, K. Murray, P. Stroobant, M. D. Watterfield and P. Riddle, *Nature* 333, 560 (1988).

E. Benveniste, J. E. Merrill (1986). *Nature* 321:610–613.

E. Benveniste, J. E. Merrill, S. E. Kaufman, D. Golde, J. Gasson (1985). *Proc. Natl. Acad. Sci. USA* 82:3930–3934.

C. Avendano, W. M. Cowan (1979). *Anat. Embryol. (Berl)* 157:347–366.

B Pettman, J. Delaunoy, J. Courageot, G. Devilliers, M. Sensenbrenner (1980). *Dev. Biol.* 75:278–287.

B. Pettman, M. Weibel, G. Daune, M. Sensenbrenner, G. Labourdette (1982). *J. Neurosci. Res.* 8:463–476.

D. Giulian, D. G. Young (1986). *J. Cell Biol.* 102:812–820.

N. Sakellaridis, D. Mangoura, A. Vernadakis (1986) *Dev. Brain Res.* 27:31–41.

T. Kurihara, Y. Tsukada (1968). *J. Neurochem.* 15:827–832.

A. D. Edgar, S. E. Pfeiffer (1985). *Dev. Neurosci.* 7:206–215.

P. M. Wood, R. P. Bunge (1986). *Nature* 320:756–758.

P. M. Wood, A. K. Williams 91984). *Dev. Brain Res.* 12:225–241.

J. Bottenstein, S. Hunter (1987). *J. Neurochem.* [suppl] 48:s44A.

S. F. Hunter, M. F. Seidel, and J. E. Bottenstein. Soc. *Neurosci. Abstr.* 13, Part 1 (1987) 194.

J. E. Bottenstein, G. Sato (1980). *Exper. Cell Res.* 129, 361.

J. E. Bottenstein (1984). "Cell Culture Methods for Molecular and Cell Biology, Volume 4: Methods for Serum Free Culture of Neuronal and Lymphoid Cells," (D. W. Barnes, D. A. Sirbasku and G. B. Sato, eds.) p.3., Alan Liss, New York.

J. E. Bottenstein, G. Sato (1979). *Proc. Natl. Acad. Sci. USA* 76:514–517.

J. J. Sedmark, S. E. Grossberg (1977). *Anal. Biochem.* 79:544–552.

J. E. Bottenstein (1986). *Adv. Biosciences* 61:3.

J. Prohaska, D. A. Clark, W. W. Wells (1973). *Anal. Biochem.* 56:275–282.

D. L. Kirk (1965). *Proc. Natl. Acad. Sci. USA* 54:1345–1353.

M. Raff, R. Mirsky, K. Fields, R. Lisak, S. Dorfman, D. Silberberg, N. Gregson, S. Leibowitz, M. C. Kennedy (1978). *Nature* 274:813–816.

J. Bottenstein (1986a). *Proc. Natl. Acad. Sci. USA* 83:1955–1959.

M. Norenberg, A. Martinez-Hernandez (1979). *Brain Res.* 161:303–310.

T. Mosmann, *J. Immunol. Meth.* 65:66, 1983.

M. Hansen, S. Nielsen, and K. Berg, *J. Immunol. Meth.* 119:203, 1989.

I. Posner, *Anal. Biochem.* 72:491, 1976.

G. Tuszynski and L. Warren, *Anal. Biochem.* 67:55, 1975.

K. Weber and D. Kuter, *J. Biol. Chem.* 246:4504, 1971.

What is claimed is:

1. A purified preparation, which is substantially free of platelet derived growth factor, of a neural progenitor regulatory factor, wherein said factor has:
   a) a molecular weight between about 40 and about 50 kilodaltons as determined by sodium dodecyl sulphate polyacrylamide gel electrophoresis; and
   b) an ability to stimulate proliferation of 0-2A glial progenitor cells.

2. A purified preparation, which is substantially free of platelet derived growth factor, of a neural progenitor cell regulatory factor, wherein said factor has the following characteristics:
   a) affinity for heparin
      i) such that said factor binds to a heparin sepharose gel particle when said factor and a preparation of heparin sepharose gel particles are mixed together with a buffer comprising about 5 mM phosphate, 50 mM NaCl, and having a pH of about 7.4 for a period of about 18 hours; and
      ii) elutes from said heparin sepharose particles when the concentration of NaCl in said buffer is raised above about 0.7M–0.8M;
   b) a molecular weight between about 40 and about 50 kilodaltons as determined by sodium dodecyl sulphate polyacrylamide gel electrophoresis; and
   c) an ability to stimulate proliferation of cells of the C62C glial cell line.

3. A purified preparation, which is substantially free of platelet derived growth factor, of a neural progenitor cell regulatory factor, wherein said factor has the following characteristics:
   a) affinity for heparin
      i) such that said factor binds to a heparin sepharose gel particle when said factor and a preparation of heparin sepharose gel particles are mixed together with a buffer comprising 5mM phosphate, 50mM NaCl, and having a pH of about 7.4 for a period of about eight hours; and
      ii) elutes from said heparin sepharose particles when the concentration of NaCl in said buffer is raised above about 0.7M–0.8M;
   b) a molecular weight between about 40 and about 50 kilodaltons as determined by sodium dodecyl sulphate polyacrylamide gel electrophoresis; and
   c) an ability to stimulate proliferation of 0-2A glial progenitor cells derived from the brain of a neonatal rat.

4. The composition of claims 1, 2 or 3 wherein said molecular weight is about 46–47 kilodaltons.

5. A purified preparation, which is substantially free of platelet derived growth factor, of a neural progenitor regulatory factor wherein said factor is the neural progenitor regulatory factor produced by a cell line ATCC (American Type Culture Collection) accession number CLR 10187 and has a molecular weight between about 40 and about 50 kilodaltons as determined by sodium dodecyl sulphate polyacrylamide gel electrophoresis.

* * * * *

UNITED STATES PATENT AND TRADEMARK OFFICE
CERTIFICATE OF CORRECTION

PATENT NO. : 5,276,145
DATED : January 4, 1994
INVENTOR(S) : Jane E. Bottenstein It is certified that error appears in the above-indentified patent and that said Letters Patent is hereby corrected as shown below:

Col. 9, ln. 12, replace "$\pm$" with -- + --.

Col. 30, ln. 58, replace "$Cm_r$ cutoff 5 kd)" with --($M_r$ cutoff 5 kd)--.

Col. 31, ln. 56, after the words "cells were" insert --fixed with 3.7% paraformaldehyde and after permeabilization--.

Col. 32, ln. 15, delete "sferrin;".

UNITED STATES PATENT AND TRADEMARK OFFICE
CERTIFICATE OF CORRECTION

PATENT NO. : 5,276,145
DATED : January 4, 1994
INVENTOR(S) : Jane E. Bottenstein It is certified that error appears in the above-indentified patent and that said Letters Patent is hereby corrected as shown below:

Col. 40, ln. 5, replace "C62C" with --C62B--.

Signed and Sealed this

Ninth Day of August, 1994

Attest:

BRUCE LEHMAN

Attesting Officer

Commissioner of Patents and Trademarks